US009132187B2

(12) United States Patent
Fachinger et al.

(10) Patent No.: US 9,132,187 B2
(45) **Date of Patent: *Sep. 15, 2015**

(54) PREVENTION AND TREATMENT OF SUB-CLINICAL PCVD

(71) Applicants: Vicky Fachinger, Bad Soden (DE); Knut Elbers, Mittelbiberach (DE); Marion Kixmoeller, Munich (DE); Francois-Xavier Orveillon, Mainz (DE); Isabelle Freiin Von Richthofen, Charlottenlund (DK); Axel Lischewski, Ockenheim (DE)

(72) Inventors: Vicky Fachinger, Bad Soden (DE); Knut Elbers, Mittelbiberach (DE); Marion Kixmoeller, Munich (DE); Francois-Xavier Orveillon, Mainz (DE); Isabelle Freiin Von Richthofen, Charlottenlund (DK); Axel Lischewski, Ockenheim (DE)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 26 days.

This patent is subject to a terminal disclaimer.

(21) Appl. No.: 13/924,811

(22) Filed: Jun. 24, 2013

(65) Prior Publication Data

US 2013/0273099 A1 Oct. 17, 2013

Related U.S. Application Data

(63) Continuation of application No. 13/079,498, filed on Apr. 4, 2011, now Pat. No. 8,496,940, which is a continuation of application No. 12/030,611, filed on Feb. 13, 2008, now Pat. No. 7,943,298.

(30) Foreign Application Priority Data

Feb. 13, 2007 (EP) .................................... 07102250

(51) Int. Cl.
*A61K 39/12* (2006.01)
*A61K 39/00* (2006.01)

(52) U.S. Cl.
CPC ......... *A61K 39/12* (2013.01); *A61K 2039/5252* (2013.01); *A61K 2039/5256* (2013.01); *A61K 2039/552* (2013.01); *C12N 2710/14143* (2013.01); *C12N 2750/10034* (2013.01)

(58) Field of Classification Search
None
See application file for complete search history.

(56) References Cited

U.S. PATENT DOCUMENTS

| | | | | |
|---|---|---|---|---|
| 5,026,543 | A * | 6/1991 | Rijke | 424/78.31 |
| 5,202,430 | A | 4/1993 | Brian et al. | |
| 5,322,774 | A | 6/1994 | Peakman et al. | |
| 5,436,001 | A | 7/1995 | Kramer | |
| 5,565,205 | A | 10/1996 | Petersen et al. | |
| 5,580,557 | A | 12/1996 | Kramer | |
| 5,733,555 | A | 3/1998 | Chu | |
| 5,885,823 | A | 3/1999 | Knittel et al. | |
| 5,925,359 | A | 7/1999 | Van Woensel et al. | |
| 5,968,525 | A | 10/1999 | Fitzgerald et al. | |
| 6,217,883 | B1 | 4/2001 | Allan et al. | |
| 6,287,856 | B1 | 9/2001 | Poet et al. | |
| 6,294,176 | B1 | 9/2001 | Cochran et al. | |
| 6,368,601 | B1 | 4/2002 | Allan et al. | |
| 6,391,314 | B1 | 5/2002 | Allan et al. | |
| 6,497,883 | B1 | 12/2002 | Bublot et al. | |
| 6,517,843 | B1 * | 2/2003 | Ellis et al. | 424/204.1 |
| 6,660,272 | B2 | 12/2003 | Allan et al. | |
| 6,703,023 | B1 | 3/2004 | Jestin et al. | |
| 6,794,163 | B2 | 9/2004 | Liu et al. | |
| 6,808,900 | B2 | 10/2004 | Simonsen | |
| 6,841,364 | B2 | 1/2005 | Yuan et al. | |
| 6,846,477 | B2 | 1/2005 | Keich et al. | |
| 6,943,152 | B1 * | 9/2005 | Audonnet et al. | 514/44 R |
| 6,953,581 | B2 | 10/2005 | Allan et al. | |
| 7,018,638 | B2 | 3/2006 | Chu et al. | |
| 7,109,025 | B1 | 9/2006 | Eloit et al. | |
| 7,122,192 | B2 | 10/2006 | Allan et al. | |
| 7,144,698 | B2 | 12/2006 | Wang et al. | |
| 7,148,015 | B2 | 12/2006 | Jestin et al. | |
| 7,169,394 | B2 | 1/2007 | Chu et al. | |
| 7,172,899 | B2 | 2/2007 | Liu et al. | |
| 7,179,472 | B2 | 2/2007 | Jestin et al. | |
| 7,192,594 | B2 | 3/2007 | Haines et al. | |
| 7,211,379 | B2 | 5/2007 | Ellis et a | |
| 7,223,407 | B2 * | 5/2007 | Jestin et al. | 424/199.1 |
| 7,223,594 | B2 | 5/2007 | Jestin et al. | |
| 7,244,433 | B2 | 7/2007 | Jestin et al. | |
| 7,258,865 | B2 | 8/2007 | Jestin et al. | |
| 7,261,898 | B2 | 8/2007 | Jestin et al. | |
| 7,273,617 | B2 | 9/2007 | Yuan et al. | |
| 7,276,353 | B2 | 10/2007 | Meng et al. | |
| 7,279,166 | B2 | 10/2007 | Meng et al. | |
| 7,297,537 | B2 | 11/2007 | Jestin et al. | |
| 7,300,785 | B2 | 11/2007 | Meerts et al. | |
| 7,312,065 | B2 | 12/2007 | Roof et al. | |
| 7,314,628 | B2 | 1/2008 | Jestin et al. | |

(Continued)

FOREIGN PATENT DOCUMENTS

| | | | |
|---|---|---|---|
| CA | 2305623 | A1 | 4/1999 |
| CN | 1579553 | A | 7/1920 |

(Continued)

OTHER PUBLICATIONS

Mahe et al. (Journal of General Virology. 2000; 81: 1815-1824).*
SEQ ID No. 3 sequence alignment with Geneseq database accession No. ABV72527 submitted Jan. 2003 in WO 2002/77210.*
SEQ ID No. 4 sequence alignment with Geneseq database accession No. ABV72527 submitted Jan. 2003 in WO 2002/77210.*
SEQ ID No. 5 sequence alignment with Geneseq database accession No. ABB99415 submitted Jan. 2003 in WO 2002/77210.*

(Continued)

*Primary Examiner* — Shanon A Foley
(74) *Attorney, Agent, or Firm* — Michael P. Morris; Wendy M. Gombert

(57) ABSTRACT

The present invention relates to the use of an immunogenic composition comprising a porcine circovirus type 2 (PCV2) antigen for the prevention and treatment of sub-clinical PCV2 infection in animals, preferably in pigs.

17 Claims, 3 Drawing Sheets

(56) References Cited

U.S. PATENT DOCUMENTS

| | | | | |
|---|---|---|---|---|
| 7,323,330 | B2 | 1/2008 | Jestin et al. | |
| 7,335,361 | B2 | 2/2008 | Liao et al. | |
| 7,358,075 | B2 | 4/2008 | Allibert et al. | |
| 7,368,117 | B2 | 5/2008 | Fetzer et al. | |
| 7,371,395 | B2 | 5/2008 | Parisot et al. | |
| 7,390,494 | B2 | 6/2008 | Jestin et al. | |
| 7,405,075 | B2 | 7/2008 | Jestin et al. | |
| 7,407,803 | B2 | 8/2008 | Jestin et al. | |
| 7,425,444 | B2 | 9/2008 | Jestin et al. | |
| 7,700,285 | B1 | 4/2010 | Eichmeyer et al. | |
| 7,758,865 | B2 | 7/2010 | Jestin et al. | |
| 7,829,101 | B2 | 11/2010 | Eichmeyer et al. | |
| 7,829,273 | B2 | 11/2010 | Roof et al. | |
| 7,829,274 | B2 | 11/2010 | Fachinger et al. | |
| 7,833,707 | B2 | 11/2010 | Eichmeyer et al. | |
| 7,838,213 | B2 | 11/2010 | Roof et al. | |
| 7,838,214 | B2 | 11/2010 | Roof et al. | |
| 7,910,306 | B2 | 3/2011 | Eichmeyer et al. | |
| 7,914,992 | B2 | 3/2011 | Fachinger et al. | |
| 7,943,298 | B2 * | 5/2011 | Fachinger et al. | 435/5 |
| 7,951,907 | B2 | 5/2011 | Jestin et al. | |
| 7,968,285 | B2 | 6/2011 | Roof et al. | |
| 8,025,888 | B2 | 9/2011 | Eichmeyer et al. | |
| 8,119,143 | B2 | 2/2012 | Roof et al. | |
| 8,475,805 | B2 | 7/2013 | Fachinger et al. | |
| 8,496,940 | B2 * | 7/2013 | Fachinger et al. | 424/204.1 |
| 8,852,613 | B2 | 10/2014 | Ohnesorge et al. | |
| 2002/0146431 | A1 | 10/2002 | Allan et al. | |
| 2003/0096377 | A1 | 5/2003 | Meng et al. | |
| 2003/0170270 | A1 | 9/2003 | Meng et al. | |
| 2003/0199581 | A1 | 10/2003 | Seligson et al. | |
| 2003/0215455 | A1 | 11/2003 | Reynolds et al. | |
| 2004/0062775 | A1 | 4/2004 | Jestin et al. | |
| 2004/0076635 | A1 | 4/2004 | Jestin et al. | |
| 2004/0091502 | A1 | 5/2004 | Jestin et al. | |
| 2004/0132178 | A1 | 7/2004 | Haines et al. | |
| 2004/0161410 | A1 | 8/2004 | Jestin et al. | |
| 2004/0208901 | A1 | 10/2004 | Ellsworth et al. | |
| 2004/0253270 | A1 | 12/2004 | Meng et al. | |
| 2004/0258715 | A1 | 12/2004 | Allan et al. | |
| 2004/0265848 | A1 | 12/2004 | Jestin et al. | |
| 2005/0008651 | A1 | 1/2005 | Jestin et al. | |
| 2005/0013823 | A1 | 1/2005 | Keich et al. | |
| 2005/0031647 | A1 | 2/2005 | Roof et al. | |
| 2005/0058653 | A1 | 3/2005 | Ellis et al. | |
| 2005/0079185 | A1 | 4/2005 | Parisot et al. | |
| 2005/0084497 | A1 | 4/2005 | Jestin et al. | |
| 2005/0147966 | A1 | 7/2005 | Meng et al. | |
| 2005/0238662 | A1 | 10/2005 | Jestin et al. | |
| 2006/0002952 | A1 | 1/2006 | Haines et al. | |
| 2006/0029617 | A1 | 2/2006 | Charreyre et al. | |
| 2006/0083756 | A1 | 4/2006 | Jestin et al. | |
| 2006/0115489 | A1 | 6/2006 | Birkett et al. | |
| 2006/0204522 | A1 | 9/2006 | Kroll et al. | |
| 2006/0222659 | A1 | 10/2006 | Jestin et al. | |
| 2006/0228373 | A1 | 10/2006 | Chu et al. | |
| 2006/0233831 | A1 | 10/2006 | Parisot et al. | |
| 2006/0246425 | A1 | 11/2006 | Allibert et al. | |
| 2006/0286123 | A1 | 12/2006 | Fetzer et al. | |
| 2007/0196879 | A1 | 8/2007 | Chabriere et al. | |
| 2008/0181910 | A1 | 7/2008 | Roof et al. | |
| 2008/0226669 | A1 | 9/2008 | Roof et al. | |
| 2008/0233147 | A1 | 9/2008 | Jestin et al. | |
| 2008/0261887 | A1 | 10/2008 | Roof et al. | |
| 2008/0267995 | A1 | 10/2008 | Roof et al. | |
| 2008/0279875 | A1 | 11/2008 | Roof et al. | |
| 2008/0279876 | A1 | 11/2008 | Roof et al. | |
| 2008/0279889 | A1 | 11/2008 | Roof et al. | |
| 2009/0016992 | A1 | 1/2009 | Eichmeyer et al. | |
| 2009/0017064 | A1 | 1/2009 | Wu et al. | |
| 2009/0022751 | A1 | 1/2009 | Eichmeyer et al. | |
| 2009/0042245 | A1 | 2/2009 | Eichmeyer et al. | |
| 2010/0136060 | A1 | 6/2010 | Kolb | |
| 2010/0184016 | A1 | 7/2010 | Lefebvre et al. | |
| 2010/0189743 | A1 | 7/2010 | Jestin et al. | |
| 2011/0033495 | A1 | 2/2011 | Roof et al. | |
| 2011/0059126 | A1 | 3/2011 | Kohler et al. | |
| 2011/0091499 | A1 | 4/2011 | Fachinger et al. | |
| 2011/0217327 | A1 | 9/2011 | Roof et al. | |
| 2011/0274710 | A1 | 11/2011 | Eichmeyer et al. | |
| 2013/0115236 | A1 | 5/2013 | Fachinger et al. | |
| 2013/0273099 | A1 * | 10/2013 | Fachinger et al. | 424/199.1 |
| 2013/0302370 | A1 | 11/2013 | Fachinger et al. | |

FOREIGN PATENT DOCUMENTS

| | | | |
|---|---|---|---|
| CN | 1458167 | A | 11/2003 |
| CN | 103122352 | A | 5/2013 |
| EP | 1050584 | A1 | 11/2000 |
| EP | 1281760 | A1 | 2/2003 |
| EP | 1386617 | A1 | 2/2004 |
| JP | 2002247979 | A | 9/2002 |
| JP | 2005511075 | A | 4/2005 |
| WO | 8906972 | A1 | 8/1989 |
| WO | 9007935 | A1 | 7/1990 |
| WO | 9118627 | A1 | 12/1991 |
| WO | 9203157 | A1 | 3/1992 |
| WO | 9316726 | A2 | 9/1993 |
| WO | 9636356 | A1 | 11/1996 |
| WO | 9918214 | A1 | 4/1999 |
| WO | 9929717 | A3 | 6/1999 |
| WO | 9929871 | A3 | 6/1999 |
| WO | 0001409 | A2 | 1/2000 |
| WO | 0047756 | A1 | 8/2000 |
| WO | 0077188 | A2 | 12/2000 |
| WO | 0077216 | A2 | 12/2000 |
| WO | 0116330 | A2 | 3/2001 |
| WO | 0117556 | A1 | 3/2001 |
| WO | 0134191 | A1 | 5/2001 |
| WO | 0145735 | A2 | 6/2001 |
| WO | 0196377 | A2 | 12/2001 |
| WO | 0249666 | A2 | 6/2002 |
| WO | 02077210 | A2 | 10/2002 |
| WO | 03003941 | A2 | 1/2003 |
| WO | 03049703 | A2 | 6/2003 |
| WO | 2004026336 | A1 | 4/2004 |
| WO | 2004058142 | A2 | 7/2004 |
| WO | 2004069184 | A2 | 8/2004 |
| WO | 2005009462 | A2 | 2/2005 |
| WO | 2005092069 | A2 | 10/2005 |
| WO | 2005112995 | A1 | 12/2005 |
| WO | 2006068663 | A2 | 6/2006 |
| WO | 2006072065 | A2 | 7/2006 |
| WO | 2006113372 | A2 | 10/2006 |
| WO | 2006113373 | A2 | 10/2006 |
| WO | 2007028823 | A1 | 3/2007 |
| WO | 2007076520 | A2 | 7/2007 |
| WO | 2007094893 | A2 | 8/2007 |
| WO | 2008073464 | A2 | 6/2008 |
| WO | 2008076915 | A2 | 6/2008 |
| WO | 2008081015 | A1 | 7/2008 |
| WO | 2008098909 | A1 | 8/2008 |
| WO | 2009030684 | A2 | 3/2009 |
| WO | 2009103037 | A1 | 8/2009 |
| WO | 2011116094 | A2 | 9/2011 |
| WO | 2014134561 | A2 | 9/2014 |

OTHER PUBLICATIONS

SEQ ID No. 5 sequence alignment with UniProt database accession No. Q9YTB6_PCV2 submitted May 1999 by Fenaux et al. In Journal of Clinical Micribiology. 2000; 38: 2494-2503).*

SEQ ID No. 6 sequence alignment with Geneseq database accession No. ADA09081 submitted Nov. 2003 in USPgPub 2003/096377.*

SEQ ID No. 6 sequence alignment with UniProt database access No. Q9YTB6_PCV2 submitted May 1999 by Fenaux et al. In Journal of Clinical Microbiology. 2000; 38: 2494-2503).*

SEQ ID No. 11 sequence alignment with Geneseq database accession No. AAO23063 submitted Oct. 2003 in WO 2003049703.*

SEQ ID No. 11 sequence alignment with UniProt database accession No. O91862_PCV2 submitted Nov. 1998 by Meehan et al. (Journal of General Virology. 1998; 79: 2171-2179).*

(56) References Cited

OTHER PUBLICATIONS

Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.
Smith et al., "Observations on Experimental Oral Infection with *Salmonella* Dublin in Calves and *Salmonella choleraesuis* in Pigs". Journal of Pathology and Bacteriology, vol. 93, No. 1, 1967, pp. 141-156.
Poppe et al., "*Salmonella typhimurium* DT104: A virulent and drug-resistant pathogen". Canadian Veterinary Journal, vol. 39, 1998, pp. 559-565.
Segalés et al., "Postweaning Multisystemic Wasting Syndrome and Porcine Circovirus Ty;e 2: The European Perspective". Trends in Emerging Viral Infections of Swine, Ch. 9.3, PMWS and PCV2: European Perspective, 2002, pp. 297-303.
Fablet et al., "A Case Study of Neonatal Diarrhoea in a Farrow-to-Finish Pig Farm". International Society for Animal Hygiene, Saint Malo, 2004, p. 151.
Dugdale et al., "Immune Response". Medline Plus Medicial Encyclopedia, Updated May 30, 2012, pp. 1-4. [Accessed at http://www.nlm.nih.gov/medlineplus/cncy/article/000821.htm on Mar. 19, 2014].
Fenaux et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2". Journal of Clinical Microbiology, vol. 38, No. 7, Jul. 2000, pp. 2494-2503.
Opriessnig et al., "A commercial vaccine based on PCV2a and an experimental vaccine based on a variant mPCV2b are both effective in protecting pigs against challenge with a 2013 U.S. variant mPCV2b strain". Vaccine, vol. 32, No. 2, 2014, pp. 230-237.
Fort et al., "Porcine circovirus type 2 (PCV2) vaccination of conventional pigs prevents viremia against PCV2 isolates of different genotypes and geographic origins". Vaccine, vol. 26, No. 8, 2008, pp. 1063-1071.
Opriessnig et al., "Differences in virulence among porcine circovirus type 2 isolates are unrelated to cluster type 2a or 2b and prior infection provides heterologous protection". Journal of General Virology, vol. 89, No. 10, 2008, pp. 2482-2491.
Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs". Journal of Virology, vol. 77, No. 20, Oct. 2003, pp. 11232-11243.
SEQ ID No. 3 Sequence Alignment with Geneseq Database Accession No. ABV72527 submitted Jan. 2003, in WO2002/077210, 3 pages.
SEQ ID No. 4 Sequence Alignment with Geneseq Database Accession No. ABV72527 submitted Jan. 2003, in WO2002/077210, 3 pages.
SEQ ID No. 5 Sequence Alignment with Geneseq Database Accession No. ABB99415, submitted Jan. 2003 in WO2002/77210, 2 pages.
SEQ ID No. 5 Sequence Alignment with UniProt Database Accession No. Q9YTB6_PCV2 Submitted May 1999 by Fenaux et al. In Journal of Clinical Microbiology, 2000; 38: 2494-2503, 2 pages.
SEQ ID No. 6 Sequence Alignment with UniProt Database Accession No. Q9YTB6_PCV2 Submitted May 1999 by Fenaux et al. In Journal of Clinical Microbiology, 2000; 38: 2494-2503, 2 pages.
SEQ ID No. 6 Sequence Alignment with Geneseq Database Accession No. ADA9081 submitted Nov. 2003 in USPgPUB 2003/096377, 2 pages.
SEQ ID No. 11 Sequence Alignment with Geneseq Database Accession No. AAO23063 submitted Oct. 2003 in WO 2003049703, 2 pages.
Lin et al., "Mycoplasma hyorhinis in Taiwan: Diagnosis and isolation of swine pneumonia pathogen". Veterinary Microbiology, vol. 115, 2006, pp. 111-116.
Harms et al., "Three cases of porcine respiratory disease complex associated with porcine circovirus type 2 infection". Journal of Swine Health and Production, vol. 10, No. 1, 2002, pp. 27-30.
Brogden, Kim A., "Polymicrobial Diseases of Animals and Humans". Polymicrobial Diseases, Chapter 1, 2002, 19 pages. [Accessed at http://www.ncbi.nlm.nih.gov/books/NBK2477/?report=printable on Jul. 8, 2014].
Opriessnig et al., "Effect of Vaccination with Selective Bacterins on Conventional Pigs Infected with Type 2 Porcine Circovirus". Veterinary Pathology, vol. 40, 2003, pp. 521-529.
Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.
Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.
Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.
Liu et al., "Bacterial Expression of an Immunologically Reactive PCV2 ORF2 Fusion Protein". 2001, Protein Expression and Purification, vol. 21, pp. 115-120.
Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.
MacKinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.
Maes et al., "Effect of vaccination against *Mycoplasma hyopneumoniae* in pig herds with an all-in/all-out production system". Vaccine, vol. 17, 1999, pp. 1024-1034.
Mahe et al., "Differential recognition of ORF2 protein from type 1 and type 2 porcine circoviruses and identification of immunorelevant epitopes". 2000, Journal of General virology, vol. 81, pp. 1815-1824.
Maranga et al., "Virus-Like Particle Production at Low Multiplicities of Infection With the Baculovirus Insect Cell System". Aug. 2003, Biotechnology and Bioengineering, vol. 84, No. 2, pp. 246-253.
Mateu et al., "A Single Amino Acid substitution Affects Multiple Overlapping Epitopes in the Major Antigenic Site of Foot-and-Mouth Disease Virus of Serotype C," Journal of General Virology, vol. 71, 1990, pp. 629-637.
McNeilly et al., "Evaluation of a Porcine Circovirus Type 2-Specific Antigen-Captive Enzyme-Linked Immunosorbent Assay for the Diagnosis of Postweaning Multisystemic Wasting Syndrome in Pigs: Comparison with Virus Isolation, Immunohistochemistry, and the Polymerase Chain Reaction", J. Vet Diagn. Invest, 2002, 14, pp. 106-112.
Minion et al., "Then Genome Sequence of Mycoplasma hyopneumoniae Strain 232, the Agent of Swine Mycoplasmosis". Nov. 2004, Journal of Bacteriology, vol. 186, No. 21, pp. 7123-7133.
Morales et al., "Serendipitous Discovery and X-Ray Structure of a Human Phosphate Binding Apolipoprotein". Mar. 2006, Structure, vol. 14, pp. 601-609.
Morris et al., "Characterization of Productive and Non-Productive ACMNPCV Infection in Selected Insect Cell Lines", Viro. 197, 1993, pp. 339-348.
Morris et al., "Promoter Influence on Baculovirus-Mediated Gene jExpression in Permissive and Nonpermissive Insect Cell Lines", J. Virol., Dec. 1992, vol. 66, No. 12, pp. 7397-7405.
Nawagitgul et al., "Open reading frame 2 of porcine circovirus type 2 encodes a major capsid protein". 2000, Journal of General Virology, vol. 81, pp. 2281-2287.
Nawagitgul et al., Modified Indirect Porcine Circovirus (PCV) Type 2-based and Recombinant Capsid Protein (ORF-2) Based Enzyme-Linked Immunosorbent Assays for Detection of Antibodies to PCV, Clinical and Diagnostic Laboratory Imunology, Ja. 2002, vol. 9, No. 1, pp. 33-40.

(56) References Cited

OTHER PUBLICATIONS

Okuda, et al., "Experimental Reproduction of Post-Weaning Multisystemic Wasting Syndrome in Cesarean-Derived, Colostrum-Deprived Piglets Inoculated with Porcine Circovirus Type 2 (PCV2): Investigation of Quantitative PCV2 Distribution and Antibody Responses", J. Vet Diagn. Invest, 2003, 15, pp. 107-114.

Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.

Opriessnig et al., "Derivation of porcine circovirus type 2-negative pigs from positive breeding herds". Journal of Swine Health and Production, vol. 12, No. 4, Jul. and Aug. 2004, pp. 186-191.

Opriessnig et al., "Experimental Reproduction of Postweaning Multisystemic Wasting Syndrome in Pigs by Dual Infection with *Mycoplasma hyopneumoniae* and Porcine Circovirus Type 2". Veterinary Pathology, vol. 41, No. 6, Nov. 2004, pp. 624-640.

Opriessnig et al., "Porcine Circovirus Type 2 Infection Decreases the Efficacy of a Modified Live Porcine Reproductive and Respiratory Syndrome Virus Vaccine", Clinical and Vaccine Immunology, Aug. 2006, vol. 13, No. 8, pp. 923-929.

Ostanello et al., "Experimental infection of 3-week-old conventional colostrum-fed pigs with porcine circovirus type 2 and porcine parvovirus". Veterinary Microbiology, vol. 108, No. 3-4, Jul. 2008, pp. 179-186.

Ponsich, A., "Etude Preliminaire De L'Impact Du Circovac Sur L'infection Par Le PCV2 En Maternite". Nov. 1981.

Portner, R., "Methods in Biotechnology"., 2007, Humana Press, Totowa, NJ, USA/.

Quintana et al., "Clinical and pathological observations on pigs with postweaning multisystemic wasting syndrome". 2001, The Veterinary Record, vol. 149, pp. 357-361.

Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.

Rueda et al., "Effect of Different Baculovirus Inactivation Procedures on the Integrity and Immunogenicity of Porcine Parvovirus-Like Particles", Vaccine, 2001, 19, pp. 726-734.

Segales et al., "Changes in Peripheral Blood Leukocyte Populations in Pigs with Natural Postweaning Multisystemic Wasting Syndrome (PMWS)", Vet. Immunology & Immunopathology, 2001, 81, pp. 37-44.

Segales et al., "Epidemiology of Porcine Circovirus Type 2 Infection: What do we Know?", Pig News & Information, 2003, vol. 24, No. 4, pp. 103N-110N.

Segales et al., "Granulomatous Enteritis and Lymphadenitis in Iberian Pigs Naturally Infected with *Lawsonia intracellularis*". Veterinary Pathology, vol. 38, No. 3, 2001, pp. 343-346.

Segales et al., "Postweaning Multisystemic Wasting Syndrome (PMWS) in Pigs, A Review", Vet. Quarterly, 2002, 24 (3), pp. 109-124.

Sequence alignment of SEQ ID No. 11 with UniProt database accession No. 091862 of Meehan et al., entered Nov. 1, 1998.

Sibila et al., "Use of a Polymerase Chain Reaction Assay and ELISA to Monitor Porcine Circovirus Type 2 Infection in Pigs From Farms with and without Postweaning Multisystemic Wasting jSyndrome", AJVR, Jan. 2004, vol. 65, No. 1, pp. 88-92.

Sorden et al., "Development of a Polyclonal-antibody-based Immunohystochemical Method for the Detection of Type 2 Porcine circovirus in Formalin-Fixed, Paraffin-Embedded Tissue", J. Vet Diagn. Inest, 1999, 11, pp. 528-530.

Thacker, Eileen L., "Mycoplasmal Diseases". Diseases of Swine, 9th Edition, Ch. 42, 2006, pp. 701-717.

Vansickle, J., "Circovirus Grips Industry". Jul. 15, 2006, National Hog Farmer.

Vasconcelos et al., "Swine and Poultry Pathogens: the Complete Genome Sequences of Two Strains of *Mycoplasma hyopneumoniae* and a Strain of *Mycoplasma synoviae*". Aug. 2005, Journal of Bacteriology, vol. 187, No. 16, pp. 5568-5577.

VIDO Swine Technical Group-Linking Knowledge to practical solutions "Vaccination Guidelines for Swine". Jun. 2004, www.vido.org.

Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.

Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.

Web site: "Does stress-free livestock mean safer food?" http://www.foodnavigator.com/Financial-Industry/Does-stress-free-livestock-mean-safer-food Accessed on: Jun. 4, 2004.

Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.

Riggs et al., "Protective Monoclonal Antibody Defines a Circumsporozoite-Like Glycoprotein Exoantigen of *Cryptosporidium parvum* Sporozoites and Merozoites". The Journal of Immunology, vol. 158, 1997, pp. 1787-1795.

Kim et al., "Efficacy of different disinfectants in vitro against porcine circovirus type 2". The Veterinary Record, vol. 164, May 2009, pp. 599-600.

Royer et al., "Susceptibility of porcine circovirus type 2 to commercial and laboratory disinfectants". Journal of Swine Health and Production, vol. 9, No. 6, 2001, pp. 281-284.

Ragona et al., "The Transcriptional Factor Egr-1 Is Synthesized by Baculovirus-Infected Insect Cells in an Active, DNA-Binding Form". DNA and Cell Biology, vol. 10, No. 1, 1991, pp. 61-66.

Rodríguez-Arrioja et al., "Dynamics of procine circovirus type 2 infection in a herd of pigs with postweaning multisystemic wasting syndrome". American Journal of Veterinary Research, vol. 63, No. 3, Mar. 2002, pp. 354-357.

Roesler et al., "Oral vaccination of pigs with an invasive gyrA-cpxA-rpoB *Salmonella typhimurium* mutant". Vaccine, vol. 23, No. 5, Dec. 2004, pp. 595-603.

Rotto, Hans "Diagnosis, Vaccination and Field Experiences with PCV-AD". Iowa Pork Progress, 2007, pp. 1-10.

Schaefer et al., "Characterization and Formulation of Multiple Epitope-Specific Neutralizing Monoclonal Antibodies for Passive Immunization against Cryptosporidiosis". Infection and Immunity, vol. 68, No. 5, May 2000, pp. 2608-2616.

Sedlik et al., "Recombinanat parvovirus-like particles as an antigen carrier: A novel nonreplicative exogenous antigen to elicit protective antiviral cytotoxic T cells". Proceedings of the National Academy of Sciences, vol. 94, Jul. 1997, pp. 7503-7508.

Segales et al., "Pathological findings associated with naturally acquired porcine circovirus type 2 associated disease". Veterinary Microbiology, vol. 98, 2004, pp. 137-149.

Segalés et al., "Immunosuppression in postweaning multisystemic wasting syndrome affected pigs". Veterinary Microbiology, vol. 98, 2004, pp. 151-158.

Segalés et al., "Porcine Circovirus Diseases". Diseases of Swine, 9th Edition, Chapter 14, Blackwell Publishing, Ames, Iowa, 2006, pp. 299-307.

Siebel, K. "PCV2 vaccination changing the pig industry Part 2. Global experiences from the field around one-shot vaccination". Pig Progress, vol. 26, No. 1, 2010, pp. 11-13.

Spier, R.E., "Multivalent Vaccines: Prospects and Challenges". Folia Microbiologica, vol. 42, No. 2, 1997, pp. 105-112.

Suradhat et al., "The influence of maternal immunity on the efficacy of a classical swine fever vaccine against classical swine fever virus, genogroup 2.2, infection". Veterinary Microbiology, vol. 92, 2003, pp. 187-194.

Thacker et al., "Effect of vaccination on the potentiation of porcine reproductive and respiratory syndrom virus (PRRSV)-induced pneumonia by *Mycoplama hyopneumoniae*". Vaccine, vol. 18, 2000, pp. 1244-1252.

Thacker, Eileen L., "Diagnosis of *Mycoplama hyopneumoniae*". Journal of Swine Health Production, vol. 12, No. 5, 2004, pp. 252-254.

(56) References Cited

OTHER PUBLICATIONS

Truong et al., "Identification of an immunorelevant ORF2 epitope from porcine circovirus type 2 as a serological marker for experimental and natural infection". Archives of Virology, vol. 146, 2001, pp. 1197-1211.
UniProt Database Accession No. O91862 submitted Nov. 1, 1998 by Meehan et al., Characterization of novel circovirus DNAs associated iwth wasting sydromes in pigs. Journal of General Virology, 1998; 79: 2171-2179, 1 page.
UniProt Database Accession No. Q9YTB6, Direct Submission, Wang et al., May 1, 1999 , 1 page.
Wan et al., "Comprehensive Prevention and Control Techniques for Porcine Circovirus Type 2 Infection". Chinese Swine Industry, No. 3, 2006, pp. 42-45.
Wang et al., "Construction and immunogenicity of recombinant adenovirus expressing the capsid protein of porcine circovirus 2 (PCV2) in mice". Vaccine, vol. 24, 2006, pp. 3374-3380.
Williams et al., "Combined vaccines and simultaneous administration: Current issues and perspectives". Annals of the New York Academy of Sciences, vol. 754, 1995, pp. xi-xv, 35-47.
Wu et al., "Replication, Integration, and Packaging of Plasmid DNA following Cotransfection with Baculovirus Viral DNA". Journal of Virology, vol. 73, No. 7, Jul. 1999, pp. 5473-5480.
Xia et al., "Preparation of and Immunity Tests with Canine Coronavirus BEI Inactivated Vaccine". Chinese Journal of Veterinary Medicine, vol. 37, No. 3, 2001, pp. 37-38.
Yamada et al., "Evaluation of the Efficacy of Inactivated Vaccine against Salmonella Enteritidis Infection in Chicken". Journal of the Japanese Society on Poultry Diseases, vol. 35, No. 1, 1999, pp. 13-21. (English Summary at p. 21).
Yuan et al., "Immunology of the porcine respiratory disease complex". Animal Science Abroad in Pigs and Poultry, No. 5, 2002, pp. 36-38.
Opriessnig et al., "A PCV2 vaccine based on genotype 2b is more effective than a 2a-based vaccine to protect against PCV2b or combined PCV2a/2b viremia in pigs with concurrent PCV2, PRRSV and PPV infection". Vaccine, vol. 31, 2013, pp. 487-494.
Beach et al., "Efficacy and future prospects of commercially available and experimental vaccines against porcine circovirus type 2 (PCV2)". Virus Research, vol. 164, 2012, pp. 33-42.
Shen et al., "Comparison of commercial and experimental porcine circovirus type 2 (PCV2) vaccines using a triple challenge with PCV2, porcine reproductive and respiratory syndrome virus (PRRSV), and porcine parvovirus (PPV)". Vaccine, vol. 28, 2010, pp. 5960-5966.
Martelli et al., "One dose of a porcine circovirus 2 subunit vaccine induces humoral and cell-mediated immunity and protects against porcine circovirus-associated disease under field conditions". Veterinary Microbiology, vol. 149, 2011, pp. 339-351.
Genbank Accession# AAF87231, PCV2 ORF2 Protein, 2000.
Gizurarson, Sveinbjörn, "Clinically Relevant Vaccine-Vaccine Interactions". BioDrugs, vol. 9, No. 6, Jun. 1998, pp. 443-453.
Groner, et al., The Biology of Baculoviruses, vol. 1, Biological Properties and Moleculary Biology, 1986, Chapter 9, Specificity and Safety of Baculoviruses, pp. 177-202.
Gualandi et al., "The Ability by Different Preparations of Porcine Parvovirus to Enhance Humoral Immunity in Swine and Guinea Pigs". Microbiologica, vol. 11, No. 4, 1988, pp. 363-369.
Gualandi et al., "The Response of Pregnant Gilts Previously Given an Inactivated Preparation of Porcine Parvovirus (PPV) to Challenge Infection with a Fully Virulent PPV". Microbiologica, vol. 15, 1992, pp. 391-396.
Ha et al., "Outbreak of salmonellosis in pigs with postweaning multisystemic wasting syndrome". Veterinary Record, vol. 156, No. 18, Apr. 2005, pp. 583-584.
Haake et al., "Influence of age on the effectiveness of PCV2 vaccination in piglets with high levels of maternally derived antibodies". Veterinary Microbiology, vol. 168, 2014, pp. 272-280.
Hamel et al., "Nucleotide Sequence of Porcine Circovirus Associated with Postweaning Multisystemic Wasting Syndrome in Pigs". Journal of Virology, vol. 72, No. 6, Jun. 1998, pp. 5262-5267.
Harding et al., "Recognizing and diagnosing postweaning multisystemic wasting syndrome (PMWS)". Swine Health and Production, vol. 5, No. 5, 1997, pp. 201-203.
Haruna et al., "The role of immunostimulation in the development of postweaning multisystemic wasting syndrome in pigs under field conditions". Canadian Journal of Veterinary Research, vol. 70, Oct. 2006, pp. 269-276.
Hilgers et al., "Alkyl-esters of polyacrylic acid as vaccine adjuvants". Vaccine, vol. 16, No. 16, 1998, pp. 1575-1581.
Hirai et al., "Dual infection with PCV-2 and porcine epidemic diarrhoea virus in neonatal piglets". The Veterinary Record, vol. 148, 2001, pp. 482-484.
Hoogland et al., "Effects of adjuvants on porcine circovirus type 2-associated lesions". Journal of Swine Health and Production, vol. 14, No. 3, 2006, pp. 133-139.
Hüser et al., "Baculovirus Vectors: Novel Mammalian Cell Gene-Delivery Vehicles and Their Applications". American Journal of Pharmacogenomics, vol. 3, No. 1, 2003, pp. 53-63.
International Search Report and Written Opinion for PCT/EP2008/051628 mailed Apr. 4, 2008.
Inumaru et al., "Expression of biologically active recombinant porcinee GM-CSF by baculovirus gene expression system". 1998, Immunology and Cell Biology, vol. 76, pp. 195-201.
Invitrogen Life Technologies, "Growth and Maintenance of Insect Cell Lines". Insect Cell Lines Manual, Version K, Jul. 12, 2002, pp. 1-34. [Accessed at http://www.med.unc.edu/pharm/sondeklab/Lab%20Resources/manuals/insect_cell_manual.pdf on Nov. 25, 2013].
Iowa State University, "typhoid Depletion: PCV2-Associated Lymphoid Depletion"., 2013, pp. 1-2. [Accessed at: http://vetmed.iastate.edu/research/labs/pcv2/pcv2-associated-disease/lymphoid-depleti . . . on Dec. 14, 2013].
Jensen et al., "Distinction between Porcine Circovirus Type 2 Enteritis and Porcine Proliferative Enteropathy caused by *Lawsonia intracellularis*". Journal of Comparative Pathology, vol. 135, 2006, pp. 176-182.
Jiang et al., "Expression, Self-Assembly, and Antigenicity of the Norwalk Virus Capsid Protein". Journal of Virology, vol. 66, No. 11, Nov. 1992, pp. 6527-6532.
Jiang et al., "Synthesis of rotavirus-Like Particles in Insect Cells: Comparative and Quantitative Analysis". Biotechnology and Bioengineering, vol. 60, No. 3, 1998, pp. 369-374.
Ju et al., "Immunogenicity of a recombinant pseudorabies virus expressing ORF1-ORF2 fusion protein of porcine circovirus type 2". 2005, Veterinary Microbiology, vol. 109, pp. 179-190.
Kamstrup, et al., "Immunisation against PCV2 structural protein by DNA vaccination of mice". 2004, Vaccine, vol. 22, pp. 1358-1361.
Kapust et al., "*Escherichia coli* maltose-binding protein is uncommonly effective at promoting the solubility of polypeptides to which it is fused". Protein Science, vol. 8, 1999, pp. 1668-1674.
Kennedy et al., "Repdocution of Lesions of Postweaning Multisystemic Wasting Syndrome by Infection of Conventional Pigs with Porcine Circovirus Type 2 Alone or in a Combination with Porcine Parvovirus". Journal of Comparative Pathology, vol. 122, 2000, pp. 9-24.
Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kim et al., "Enteritis associated with procine circovirus 2 in pigs". 2004, The Canadian Journal of Veterinary Research, vol. 68, pp. 218-221.
Kiupel, M. "Postweaning Multisystemic Wasting Syndrome (PMWS) in pigs". Production diseases in Farm Animals, 12th International Conference, Section D, Wageningen Academic Publishers, The Netherlands, 2006, pp. 74-89.

(56) References Cited

OTHER PUBLICATIONS

Kixmoller et al., "Reduction of PMWS-associated clinical signs and co-infections by vaccination against PCV2". 2008, Vaccine, vol. 26, pp. 3443-3451.
Kost, et al., "Recombinant baculoviruses as mammalian cell gene-delivery vectors". Apr. 2002, Trends in Biotechnology, vol. 20, No. 4, pp. 173-180.
Kovacs et al., "The live attenuated bovine viral diarrhea virus components of a multi-valent vaccine confer protection against fetal infection". Veterinary Microbiology, vol. 96, 2003, pp. 117-131.
Kyriazakis et al., "The Maintenance of Health". Whittemore's Science and Practice of Pig Production, Third Edition, Chapter 7, Blackwell Publishing Ltd., Oxford, UK, 2006, pp. 263-316.
Lekcharoensuk et al., "Epitope Mapping of the Major Capsid Protein of Type 2 Porcine Circovirus (PCV2) by Using Chimeric PCV1 and PCV2". Journal of Virology, vol. 78, No. 15, Aug. 2004, pp. 8135-8145.
Li et al., "Expression and Self-Assembly of Empty Virus-Like Particle of Hepatitis E Virus". Journal of Virology, vol. 71, No. 10, Oct. 1997, pp. 7207-7213.
Liu et al., "Development of an ELISA Baed on the Baculovirus-Expressed Capsid Protein of Porcine Circovirus Type 2 as Antigen". Journal of Veterinary Medical Science, vol. 66, No. 3, Mar. 2004, pp. 237-242.
McKeown et al., "Effects of Porcine Circovirus Type 2 (PCV2) Maternal Antibodies on Experimental Infection of Piglets with PCV2". Clinical and Diagnostic Laboratory Immunology, vol. 12, No. 11, Nov. 2005, pp. 1347-1351.
Meehan et al., "Characterization of novel circovirus DNAs associated with wasting syndromes in pigs". Journal of General Virology, vol. 79, 1998, pp. 2171-2179.
Mortola et al., "Efficient assembly and release of SARS coronavirus-like particles by a heterologous expression system". FEBS Letters, vol. 576, 2004, pp. 174-178.
Muirhead, Mike, "Sources of information on PMWS/PDNS". The Veterinary Record, vol. 150, No. 14, Apr. 6, 2002, p. 456.
Murakami et al., "Occurrence of Swine Salmonellosis in Postweaning Multisystemic Wasting Syndrome (PMWS) Affected Pigs Concurrently Infected with Porcine Reproduction and Respiratory Syndrome Virus (PRRSV)". Journal of Veterinary Medical Science, vol. 68, 2006, pp. 387-391.
Neutra et al., "Optimization of protein-production by the baculovirus expression vector system in shake flasks". Applied Microbiology and Biotechnology Journal, vol. 37, No. 1, 1992, pp. 74-78.
Noad et al., "Virus-like particles as immunogens" Trends in Microbiology, vol. 11, No. 9, Sep. 2003, pp. 438-444.
Ohnesorge et al., "Efficacy Studies- Efficacy evaluation of a mixed *Mycoplasma hyopneumoniae* bacterin and a porcine circovirus type 2 vaccine". 2007, 1 page. [Accessed at http://www.ingelvacflex.co.uk/mycoflex/research/efficacy.php on Jul. 31, 2012].
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, 2002, pp. 11837-11844.
Opriessnig et al., "Effect of porcine circovirus type 2 (PCV2) vaccination on porcine reproductive and respiratory syndrome virus (PRRSV) and PCV2 coinfection". Veterinary Microbiology, vol. 131, 2008, pp. 103-114.
Opriessnig et al., "Experimental Co-Infection with Porcine Circovirus Type 2 and *Salmonella typhimurium* or *Lawsonia intracellularis*". Pig Progress, Jun. 2008, 1 page. [Accessed at: http://www.pigprogress.net/public/file/IPVS-oral%20presentations/Viral%20diseases/Experimental%20co-infection%20with%20PCV2%20and%20salmonella%20Typhimurium%20or%20lawsonia%20intracellularis.pdf on Mar. 17, 2010].
Paterson, J.E., "Health and antimicrobial resistance". Manipulating Pig Production X, Chapter 2, Proceedings of the Tenth Biennial Conference of the Australasian Pig Science Association (Inc.) (APSA) held in Christchurch, New Zealand on Nov. 27-30, 2005, Werribee, Victoria, Australia: Australasian Pig Association (Inc.), pp. 21-74.
Patterson et al., "Baculovirus and Insect Cell Gene Expression: Review of Baculovirus Biotechnology". Environmental Health Perspectives, vol. 103, Nos. 7-8, Jul.-Aug. 1995, pp. 756-759.
"Calendar, Mar. 2007". 3rd Annual Pig Veterinary Society Congress, vol. 37, No. 2, 2007, p. 33. [Accessed at http://www.piginternational-digital.com/piginternationa1/2007013//Print . . . on Aug. 3, 2012].
"General Methods 6xHis and GST Purification Direct Cloning". Baculovirus Expression Vector System Manual, 6th Edition, May 1999, pp. 1-108.
"H-V11-Postweaning multisystemic wasting syndrome-Lymph node- Pig". Read-Only Case Details Reviews: Mar. 2009, pp. 1-4. [Accessed at http://www.askjpc.org/vspo/show_page.php?id=800 on Dec. 14, 2013].
9 C.F.R. § 113.35 (2010).
Abstract in English of CN1458167, dated Nov. 26, 2003.
Albina et al., "An Experimental Model for Post-weaning Multisystenic Wasting Syndrome (PMWS) in Growing Piglets". 2001, Journal of Comparative Pathology, vol. 123, pp. 292-303.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allan et al., "Letters, Immunostiulations, PCV-2 and PMWS", The Vet. Records, Aug. 5, 2000, pp. 170-171.
Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.
Allan et al., "PCV2; ticking time bomb?" Pig Progress, vol. 18, No. 5, 2002, pp. 14-12.
Allan et al., "PMWS/PCVD: Diagnosis, Disease, and Control: What do we know?" 2006, Proceedings of the 19th IPVS Congress, Copenhagen, Denmark, vol. 1, pp. 1-9.
Allan et al., "Porcine Circoviruses; A Review", J. Vet., Diagn. Invest. 2000, 12, pp. 3-14.
Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.
Allan et al., Guest Editorial, "PCV-2 Infection in Swine; More Than Just Postweaning Multisystemic Wasting Syndrome", The Vet Journ., 2003, 166, pp. 222-223.
Bahnemann, Hans G., "Inactivation of Viruses in Serum with Binary Ethyleneimine". Journal of Clinical Microbiology, vol. 3, No. 2, Feb. 1976, pp. 209-210.
Banholzer, E. "A Follow-Up: PCV2, PRRS, *Mycoplasma hyopneumoniae,* Improvac". IPVS Congress, Jul. 16-19, 2006, pp. 1-20.
Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.
Begue et al., "Future Combined Vaccines". Journal of Infectious Diseases, vol. 173, Supp 3, 1996, pp. S295-S297.
Beseme et al., "Vaccination strategies for the control of circoviral diseases in pigs: PMWS and PCV2-associated PRDC". Proceedings of the Japanese Pig Veterinary Society, vol. 49, 2006, pp. 15-38.
Blanchard et al., "An ORF2 protein-based ELISA for porcine circovirus type 2 antibodies in post-weaning multisystemic wasting syndrome". Veterinary Microbiology, vol. 94, 2003, pp. 183-194.
Blanchard et al., "Protection of swine against post-weaning multisystemic wasting syndrome (PMWS) by porcine circovirus type 2 (PCV2) proteins". Vaccine, vol. 21, 2003, pp. 4565-4575.
Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletion, www.bi-vetmedica.com/swine-research/MycoFLEX-Mycoplasma-immunity_TB2.pdf; 14 pages.

(56) References Cited

OTHER PUBLICATIONS

Boehringer Ingelheim Vetmedica, Inc., Ingelvacâ Circoflexâ Material Safety Data Sheet, Online Oct. 2006, pp. 1-10, URL:http://bi-vetmedica.com/sites/default/files/ingelvac-circoflex-msds.pdf.
Boisseson et al., “Molecular characterization of Porcine circovirus type 2 isolates from post-weaning multisystemic wasting syndrome-affected and non-affected pigs”. 2004, Journal of General Virology, vol. 85, pp. 293-304.
Bolin et al., “Postweaning multisystemic wasting syndrome induced after experimental inoculation of cesarean-derived, colostrum-deprived piglets with type 2 porcine circovirus”. 2001, Journal of Veterinary Diagnostice Investigation, vol. 13, pp. 185-194.
Bowie, et al., “Deciphering the Message in Protein Sequences: Tolerance to Amino Acid Substitutions,” Science, vol. 247, 1990, pp. 1306-1310.
Caprioli et al., “PCR detection of porcine circovirus type 2 (PCV2) DNA in blood, tonsillar and faecal swabs from experimentally infected pigs”. Research in Veterinary Sciences, vol. 81, No. 2, Oct. 2006, pp. 287-292.
Chae, C. “A review of porcine circovirus 2-associated syndromes and diseases”. The Veterinary Journal, vol. 169, No. 3, 2005, pp. 326-336.
Chae, C., “Postweaning multisystemic wasting syndrome: a review of aetiology, diagnosis and pathology”. 2004, The Veterinary Journal, vol. 168, pp. 41-49.
Charbonneau, G., “Canadian Experiences with Porcine Circovirus Associated Disease”. 2007, Iowa Pork Congress; 30 pages.
Chen et al., “Serological survey of serum antibodies against porcine circovirus type 2 (PCV2) in swine, chicken, duck, goat and cattle fromZhejiang province, China”. Revue de Médecine Vétérinaire, vol. 158, Nos. 8-9, 2007, pp. 458-462.
Cheung et al., “Kinetics of Porcine Circovirus Type 2 Replication”. Archives of Virology, vol. 147, 2002, pp. 43-58.
Chevez et al., “Long-term analysis of PCV2 prevalence in a Mexican herd using Ingelvac CircoFLES®”. 22nd International Pig Veterinary Society Congress, Virology and Viral Diseases-PCV2, 2012, p. 908.
Chiou, et al., “The Effect of Porcine Circovirus Infection on the Immune Response of Pigs After Vaccination Against Classical Swine Fever and Pseudorabies”. 2006, Proceedings of the 19th IPVS Congress, Copenhagen, Denmark, p. 79.
Chung et al., “Real-time PCR for quantitation of porcine reproductive and respiratory syndrome virus and porcine circovirus type 2 in naturally-infected and challenged pigs”. Journal ofVirological Methods , vol. 124, 2005, pp. 11-19.
Czermak et al., “Membrane Filtration in Animal Cell Cutlure”. 2007, Methods in Biotechnology, vol. 24, pp. 397-420, Humana Press, New Jersey, USA.
Darwich et al., “Cytokine profiles of peripheral blood mononuclear cells from pigs with postweaning multisystemic wasting syndrome in response to mitogen, superantigen or recall viral antigens”. 2003, Journal of General Virology, vol. 84, pp. 3453-3457.
Dawson et al., “Studies of the field efficacy and safety of a single-dose *Mycoplasma hyopneumoniae* vaccine for pigs”. Veterinary Record, vol. 151, 2002, pp. 535-538.
Ellis et al., “Lack of antibodies to porcine circovirus type 2 virus in beef and dairy cattle and horses in western Canada”. Canadian Veterinary Journal, vol. 42, 2001, pp. 461-464.
Ellis et al., “Porcine circovirus-2 and concurrent infections in the field”. Veterinary Microbiology, vol. 98, No. 2, Feb. 2004, pp. 159-163.
Ellis, John A., “Porcine circovirus: An old virus in a new guise causes an emerging disease thorugh a novel pathogenesis”. Large Animal Veterinary Rounds, vol. 3, No. 4, Apr. 2003, pp. 1-6.
European Search Report (Supplementary) for EP07867723 dated May 20, 2010.
Fachinger et al., “The effect of vaccination against porcine circovirus type 2 in pigs suffering from porcine respiratory disease complex”. 2008, Vaccine, vol. 26, pp. 1488-1499.
Fan et al., “Immunogenicity of Empty Capsids of Porcine Circovirus Type 2 Produced in Insect Cells”. 2007, Veterinary Research Communications, vol. 31, pp. 487-496.
Fan et al., “Preclinical study of influenza virus A M2 peptide conjugate vaccines in mice, ferrets, and rhesus monkeys”. Vaccine, vol. 22, 2004, pp. 2993-3003.
Fan et al., “The Expression of Porcine Circovirus Type 2 ORF2 Gene in Insect Cells and its Character”. Chinese Journal of Biotechnology, vol. 21, No. 6, Nov. 2005, pp. 975-978.
Fenaux et al., “A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs”, J. Virol, Jun. 2004, vol. 78, No. 12, pp. 6297-6303.
Gagrcin et al., “Complex of Swine Respiratory Diseases-Strategy of control in light of latest knowledge”. Veterinarski Glasnik, vol. 58, No. 7-8, 2004, pp. 409-418. [English Abstract at p. 417.].
Genbank Accession No. AAC61738, Version AAC61738.1 GI:3661517, Sep. 29, 1998.
GenBank Accession No. AF201311, Direct Submission, submitted Feb. 23, 2000 in Mankertz et al., “Characterization of PCV-2 isolates from Spain, Germany and France”, Virus Research, vol. 66, No. 1, 2000, pp. 65-77, 2 pages.
EMBL Acession No. ACA49867, Wang et al., “Porcine circovirus-2 capside protein”., Mar. 5, 2008, 1 page.
EMBL Acession No. ACA49861, Wang et al., “Porcine circovirus-2 capside protein”., Mar. 5, 2008, 1 page.
EMBL Acession No. ACV53224, Cortey et al., “Porcine circovirus-2 partial capsid protein”., Sep. 13, 2009, 1 page.
Opriessnig et al., “Effect of porcine parvovirus vaccination on the development of PMWS in segregated early weaned pigs coinfected with type 2 porcine circovirus and porcine parvovirus”. Veterinary Microbiology, vol. 98, 2004, pp. 209-220.

* cited by examiner

SEQUENCE LISTING

<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence.

<400> SEQUENCE: 1 ccgccatg 8

<210> SEQ ID NO 2
<211> LENGTH: 6
<212> TYPE: DNA
<213> ORGANISM: Artificial Sequence
<220> FEATURE:

-continued

<223> OTHER INFORMATION: This is a recombinant Eco R1 sequence.

<400> SEQUENCE: 2 gaattc 6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc 60
ttggccagat cctccgccgc cgcccctggc tcgtccaccc ccgccaccgc taccgttgga 120
gaaggaaaaa tggcatcttc aacacccgcc tctcccgcac cttcggatat actgtggaga 180
aggaaaaatg gcatcttcaa cacccgcctc tcccgcacct tcggatatac tgtgacgact 240
ttgttccccc gggagggggg accaacaaaa tctctatacc ctttgaatac tacagaataa 300
gaaaggttaa ggttgaattc tggccctgct cccccatcac ccagggtgat aggggagtgg 360
gctccactgc tgttattcta gatgataact ttgtaacaaa ggccacagcc ctaacctatg 420
acccatatgt aaactactcc tcccgccata caatccccca acccttctcc taccactccc 480
gttacttcac acccaaacct gttcttgact ccactattga ttacttccaa ccaaataaca 540
aaaggaatca gctttggctg aggctacaaa cctctagaaa tgtggaccac gtaggcctcg 600
gcactgcgtt cgaaaacagt aaatacgacc aggactacaa tatccgtgta accatgtatg 660
tacaattcag agaatttaat cttaaagacc ccccacttaa accctaaatg aat 713

<210> SEQ ID NO 4
<211> LENGTH: 713
<212> TYPE: DNA
<213> ORGANISM: Porcine circovirus

<400> SEQUENCE: 4
ccgccatgac gtatccaagg aggcgttacc gcagaagaag acaccgcccc cgcagccatc 60
ttggccagat cctccgccgc cgcccctggc tcgtccaccc ccgccaccgc taccgttgga 120
gaaggaaaaa tggcatcttc aacacccgcc tctcccgcac cttcggatat actgtcaagg 180
ctaccacagt cacaacgccc tcctgggcgg tggacatgat gagatttaat attgacgact 240
ttgttccccc gggagggggg accaacaaaa tctctatacc ctttgaatac tacagaataa 300
gaaaggttaa ggttgaattc tggccctgct cccccatcac ccagggtgat aggggagtgg 360
gctccactgc tgttattcta gatgataact ttgtaacaaa ggccacagcc ctaacctatg 420
acccatatgt aaactactcc tcccgccata caatccccca acccttctcc taccactccc 480
gttacttcac acccaaacct gttcttgact ccactattga ttacttccaa ccaaataaca 540
aaaggaatca gctttggctg aggctacaaa cctctagaaa tgtggaccac gtaggcctcg 600
gcactgcgtt cgaaaacagt aaatacgacc aggactacaa tatccgtgta accatgtatg 660
tacaattcag agaatttaat cttaaagacc ccccacttga accctaagaa ttc 713

<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Arg Tyr Arg Arg Arg Arg His Arg Pro Arg

-continued 1 5 10 15

Ser His Leu Gly Gln Ile Leu Arg Arg Arg Pro Trp Leu Val His Pro
20 25 30

Arg His Arg Tyr Arg Trp Arg Arg Lys Asn Gly Ile Phe Asn Thr Arg
35 40 45

Leu Ser Arg Thr Phe Gly Tyr Thr Val Lys Ala Thr Thr Val Thr Thr
50 55 60

Pro Ser Trp Ala Val Asp Met Met Arg Phe Asn Ile Asp Asp Phe Val
65 70 75 80

Pro Pro Gly Gly Gly Thr Asn Lys Ile Ser Ile Pro Phe Glu Tyr Tyr
85 90 95

Arg Ile Arg Lys Val Lys Val Glu Phe Trp Pro Cys Ser Pro Ile Thr
100 105 110

Gln Gly Asp Arg Gly Val Gly Ser Thr Ala Val Ile Leu Asp Asp Asn
115 120 125

Phe Val Thr Lys Ala Thr Ala Leu Thr Tyr Asp Pro Tyr Val Asn Tyr
130 135 140

Ser Ser Arg His Thr Ile Pro Gln Pro Phe Ser Tyr His Ser Arg Tyr
145 150 155 160

Phe Thr Pro Lys Pro Val Leu Asp Ser Thr Ile Asp Tyr Phe Gln Pro
165 170 175

Asn Asn Lys Arg Asn Gln Leu Trp Leu Arg Leu Gln Thr Ser Arg Asn
180 185 190

Val Asp His Val Gly Leu Gly Thr Ala Phe Glu Asn Ser Lys Tyr Asp
195 200 205

Gln Asp Tyr Asn Ile Arg Val Thr Met Tyr Val Gln Phe Arg Glu Phe
210 215 220

Asn Leu Lys Asp Pro Pro Leu Lys Pro
225 230

<210> SEQ ID NO 6
<211> LENGTH: 233
<212> TYPE: PRT
<213> ORGANISM: Porcine circovirus

<400> SEQUENCE: 6

Met Thr Tyr Pro Arg Arg Arg Tyr Arg Arg Arg Arg His Arg Pro Arg
1 5 10 15

Ser His Leu Gly Gln Ile Leu Arg Arg Arg Pro Trp Leu Val His Pro
20 25 30

Arg His Arg Tyr Arg Trp Arg Arg Lys Asn Gly Ile Phe Asn Thr Arg
35 40 45

Leu Ser Arg Thr Phe Gly Tyr Thr Val Lys Ala Thr Thr Val Thr Thr
50 55 60

Pro Ser Trp Ala Val Asp Met Met Arg Phe Asn Ile Asp Asp Phe Val
65 70 75 80

Pro Pro Gly Gly Gly Thr Asn Lys Ile Ser Ile Pro Phe Glu Tyr Tyr
85 90 95

Arg Ile Arg Lys Val Lys Val Glu Phe Trp Pro Cys Ser Pro Ile Thr
100 105 110

Gln Gly Asp Arg Gly Val Gly Ser Thr Ala Val Ile Leu Asp Asp Asn
115 120 125

Phe Val Thr Lys Ala Thr Ala Leu Thr Tyr Asp Pro Tyr Val Asn Tyr
130 135 140

-continued

```
Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230


<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7

gcggccgcgg gaattcgatc cgccatgacg tatccaagga ggcgttaccg cagaagaaga      60

caccgccccc gcagccatct tggccagatc ctccgccgcc gcccctggct cgtccacccc     120

cgccaccgct accgttggag aaggaaaaat ggcatcttca acacccgcct ctcccgcacc     180

ttcggatata ctgtcaaggc taccacagtc acaacgccct cctgggcggt ggacatgatg     240

agatttaata ttgacgactt tgttcccccg ggagggggga ccaacaaaat ctctataccc     300

tttgaatact acagaataag aaaggttaag gttgaattct ggccctgctc ccccatcacc     360

cagggtgata ggggagtggg ctccactgct gttattctag atgataactt tgtaacaaag     420

gccacagccc taacctatga cccatatgta aactactcct cccgccatac aatcccccaa     480

cccttctcct accactcccg ttacttcaca cccaaacctg ttcttgactc cactattgat     540

tacttccaac caaataacaa aaggaatcag ctttggctga ggctacaaac ctctagaaat     600

gtggaccacg taggcctcgg cactgcgttc gaaaacagta aatacgacca ggactacaat     660

atccgtgtaa ccatgtatgt acaattcaga gaatttaatc ttaaagaccc ccccacttgaa     720

ccctaagaat tctatcacta gtgaattcgc ggccgc                               756


<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2,
      ORF-2construct, which includes baculovirus and pGEM T-easy
      coding sequences.

<400> SEQUENCE: 8

aagctttact cgtaaagcga gttgaaggat catatttagt tgcgtttatg agataagatt      60

gaaagcacgt gtaaaatgtt tcccgcgcgt tggcacaact atttacaatg cggccaagtt     120

ataaaagatt ctaatctgat atgttttaaa acacctttgc ggcccgagtt gtttgcgtac     180

gtgactagcg aagaagatgt gtggaccgca gaacagatag taaaacaaaa ccctagtatt     240

ggagcaataa tcgatttaac caacacgtct aaatattatg atggtgtgca ttttttgcgg     300

gcgggcctgt tatacaaaaa aattcaagta cctggccaga ctttgccgcc tgaaagcata     360
```

-continued

```
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gtttttacga agcgatgaca   2520
tgacccccgt agtgacaacg atcacgccca aaagaactgc cgactacaaa attaccgagt   2580
atgtcggtga cgttaaaact attaagccat ccaatcgacc gttagtcgaa tcaggaccgc   2640
tggtgcgaga agccgcgaag tatggcgaat gcatcgtata acgtgtggag tccgctcatt   2700
```

-continued

```
agagcgtcat gtttagacaa gaaagctaca tatttaattg atcccgatga ttttattgat   2760
aaattgaccc taactccata cacggtattc tacaatggcg ggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga aagaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaaccacca aactgccaaa aaatgaaaac tgtcgacaag   3240
ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
catttgtagt attatctata attgaaaacg cgtagttata atcgctgagg taatatttaa   3420
aatcattttc aaatgattca cagttaattt gcgacaatat aattttattt tcacataaac   3480
tagacgcctt gtcgtcttct tcttcgtatt ccttctcttt ttcatttttc tcctcataaa   3540
aattaacata gttattatcg tatccatata tgtatctatc gtatagagta aatttttttgt   3600
tgtcataaat atatatgtct tttttaatgg ggtgtatagt accgctgcgc atagtttttc   3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tcccttttct atactattgt   3900
ctgcgagcag ttgtttgttg ttaaaaataa cagccattgt aatgagacgc acaaactaat   3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atcagatctg   4140
cagcggccgc gggaattcga tccgccatga cgtatccaag gaggcgttac cgcagaagaa   4200
gacaccgccc ccgcagccat cttggccaga tcctccgccg ccgcccctgg ctcgtccacc   4260
cccgccaccg ctaccgttgg agaaggaaaa atggcatctt caacacccgc ctctcccgca   4320
ccttcggata tactgtcaag gctaccacag tcacaacgcc ctcctgggcg gtggacatga   4380
tgagatttaa tattgacgac tttgttcccc cgggaggggg gaccaacaaa atctctatac   4440
cctttgaata ctacagaata agaaaggtta aggttgaatt ctggccctgc tcccccatca   4500
cccagggtga taggggagtg ggctccactg ctgttattct agatgataac tttgtaacaa   4560
aggccacagc cctaacctat gacccatatg taaactactc ctcccgccat acaatccccc   4620
aacccttctc ctaccactcc cgttacttca cacccaaacc tgttcttgac tccactattg   4680
attacttcca accaaataac aaaaggaatc agctttggct gaggctacaa acctctagaa   4740
atgtggacca cgtaggcctc ggcactgcgt tcgaaaacag taaatacgac caggactaca   4800
atatccgtgt aaccatgtat gtacaattca gagaatttaa tcttaaagac ccccccacttg   4860
aaccctaaga attctatcac tagtgaattc gcggccgccg gccgctccag aattctagaa   4920
ggtacccggg atcctttcct gggacccggc aagaaccaaa aactcactct cttcaaggaa   4980
atccgtaatg ttaaacccga cacgatgaag cttgtcgttg gatggaaagg aaaagagttc   5040
tacagggaaa cttggacccg cttcatggaa gacagcttcc ccattgttaa cgaccaagaa   5100
```

```
gtgatggatg ttttccttgt tgtcaacatg cgtcccacta gacccaaccg ttgttacaaa   5160
ttcctggccc aacacgctct gcgttgcgac cccgactatg tacctcatga cgtgattagg   5220
atcgtcgagc cttcatgggt gggcagcaac aacgagtacc gcatcagcct ggctaagaag   5280
ggcggcggct gcccaataat gaaccttcac tctgagtaca ccaactcgtt cgaacagttc   5340
atcgatcgtg tcatctggga gaacttctac aagcccatcg tttacatcgg taccgactct   5400
gctgaagagg aggaaattct ccttgaagtt tccctggtgt tcaaagtaaa ggagtttgca   5460
ccagacgcac ctctgttcac tggtccggcg tattaaaaca cgatacattg ttattagtac   5520
atttattaag cgctagattc tgtgcgttgt tgatttacag acaattgttg tacgtatttt   5580
aataattcat taaatttata atctttaggg tggtatgtta gagcgaaaat caaatgattt   5640
tcagcgtctt tatatctgaa tttaaatatt aaatcctcaa tagatttgta aaataggttt   5700
cgattagttt caaacaaggg ttgtttttcc gaaccgatgg ctggactatc taatggattt   5760
tcgctcaacg ccacaaaact tgccaaatct tgtagcagca atctagcttt gtcgatattc   5820
gtttgtgttt tgttttgtaa taaaggttcg acgtcgttca aaatattatg cgcttttgta   5880
tttctttcat cactgtcgtt agtgtacaat tgactcgacg taaacacgtt aaataaagct   5940
tggacatatt taacatcggg cgtgttagct ttattaggcc gattatcgtc gtcgtcccaa   6000
ccctcgtcgt tagaagttgc ttccgaagac gattttgcca tagccacacg acgcctatta   6060
attgtgtcgg ctaacacgtc cgcgatcaaa tttgtagttg agctttttgg aattatttct   6120
gattgcgggc gtttttgggc gggtttcaat ctaactgtgc ccgattttaa ttcagacaac   6180
acgttagaaa gcgatggtgc aggcggtggt aacatttcag acggcaaatc tactaatggc   6240
ggcggtggtg gagctgatga taaatctacc atcggtggag gcgcaggcgg ggctggcggc   6300
ggaggcggag gcggaggtgg tggcggtgat gcagacggcg gtttaggctc aaatgtctct   6360
ttaggcaaca cagtcggcac ctcaactatt gtactggttt cgggcgccgt ttttggtttg   6420
accggtctga gacgagtgcg attttttttcg tttctaatag cttccaacaa ttgttgtctg   6480
tcgtctaaag gtgcagcggg ttgaggttcc gtcggcattg gtggagcggg cggcaattca   6540
gacatcgatg gtggtggtgg tggtggaggc gctggaatgt taggcacggg agaaggtggt   6600
ggcggcggtg ccgccggtat aatttgttct ggtttagttt gttcgcgcac gattgtgggc   6660
accggcgcag gcgccgctgg ctgcacaacg gaaggtcgtc tgcttcgagg cagcgcttgg   6720
ggtggtggca attcaatatt ataattggaa tacaaatcgt aaaaatctgc tataagcatt   6780
gtaatttcgc tatcgtttac cgtgccgata tttaacaacc gctcaatgta agcaattgta   6840
ttgtaaagag attgtctcaa gctcgccgca cgccgataac aagccttttc atttttacta   6900
cagcattgta gtggcgagac acttcgctgt cgtcgacgta catgtatgct ttgttgtcaa   6960
aaacgtcgtt ggcaagcttt aaaatattta aaagaacatc tctgttcagc accactgtgt   7020
tgtcgtaaat gttgttttttg ataatttgcg cttccgcagt atcgacacgt tcaaaaaatt   7080
gatgcgcatc aattttgttg ttcctattat tgaataaata agattgtaca gattcatatc   7140
tacgattcgt catggccacc acaaatgcta cgctgcaaac gctggtacaa ttttacgaaa   7200
actgcaaaaa cgtcaaaact cggtataaaa taatcaacgg gcgctttggc aaaatatcta   7260
ttttatcgca caagcccact agcaaattgt atttgcagaa aacaatttcg gcgcacaatt   7320
ttaacgctga cgaaataaaa gttcaccagt taatgagcga ccacccaaat tttataaaaa   7380
tctattttaa tcacggttcc atcaacaacc aagtgatcgt gatggactac attgactgtc   7440
```

-continued

```
ccgatttatt tgaaacacta caaattaaag gcgagctttc gtaccaactt gttagcaata   7500
ttattagaca gctgtgtgaa gcgctcaacg atttgcacaa gcacaatttc atacacaacg   7560
acataaaact cgaaaatgtc ttatatttcg aagcacttga tcgcgtgtat gtttgcgatt   7620
acggattgtg caaacacgaa aactcactta gcgtgcacga cggcacgttg gagtatttta   7680
gtccggaaaa aattcgacac acaactatgc acgtttcgtt tgactggtac gcggcgtgtt   7740
aacatacaag ttgctaacgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggcgctct tccgcttcct cgctcactga ctcgctgcgc tcggtcgttc ggctgcggcg   8040
agcggtatca gctcactcaa aggcggtaat acggttatcc acagaatcag gggataacgc   8100
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata aagataccag gcgtttcccc ctggaagctc   8280
cctcgtgcgc tctcctgttc cgaccctgcc gcttaccgga tacctgtccg cctttctccc   8340
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
tagcggtggt ttttttgttt gcaagcagca gattacgcgc agaaaaaaag gatctcaaga   8760
agatcctttg atcttttcta cggggtctga cgctcagtgg aacgaaaact cacgttaagg   8820
gattttggtc atgagattat caaaaaggat cttcacctag atccttttaa attaaaaatg   8880
aagttttaaa tcaatctaaa gtatatatga gtaaacttgg tctgacagtt accaatgctt   8940
aatcagtgag gcacctatct cagcgatctg tctatttcgt tcatccatag ttgcctgact   9000
ccccgtcgtg tagataacta cgatacggga gggcttacca tctggcccca gtgctgcaat   9060
gataccgcga gacccacgct caccggctcc agatttatca gcaataaacc agccagccgg   9120
aagggccgag cgcagaagtg gtcctgcaac tttatccgcc tccatccagt ctattaattg   9180
ttgccgggaa gctagagtaa gtagttcgcc agttaatagt ttgcgcaacg ttgttgccat   9240
tgctacaggc atcgtggtgt cacgctcgtc gtttggtatg gcttcattca gctccggttc   9300
ccaacgatca aggcgagtta catgatcccc catgttgtgc aaaaaagcgg ttagctcctt   9360
cggtcctccg atcgttgtca gaagtaagtt ggccgcagtg ttatcactca tggttatggc   9420
agcactgcat aattctctta ctgtcatgcc atccgtaaga tgcttttctg tgactggtga   9480
gtactcaacc aagtcattct gagaatagtg tatgcggcga ccgagttgct cttgcccggc   9540
gtcaatacgg gataataccg cgccacatag cagaacttta aaagtgctca tcattggaaa   9600
acgttcttcg gggcgaaaac tctcaaggat cttaccgctg ttgagatcca gttcgatgta   9660
acccactcgt gcacccaact gatcttcagc atcttttact ttcaccagcg tttctgggtg   9720
agcaaaaaca ggaaggcaaa atgccgcaaa aaagggaata agggcgacac ggaaatgttg   9780
aatactcata ctcttccttt ttcaatatta ttgaagcatt tatcagggtt attgtctcat   9840
```

-continued

```
gagcggatac atatttgaat gtatttagaa aaataaacaa ataggggttc cgcgcacatt   9900

tccccgaaaa gtgccacctg acgtctaaga aaccattatt atcatgacat taacctataa   9960

aaataggcgt atcacgaggc cctttcgtct cgcgcgtttc ggtgatgacg gtgaaaacct  10020

ctgacacatg cagctcccgg agacggtcac agcttgtctg taagcggatg ccgggagcag  10080

acaagcccgt cagggcgcgt cagcgggtgt tggcgggtgt cggggctggc ttaactatgc  10140

ggcatcagag cagattgtac tgagagtgca ccatatgcgg tgtgaaatac cgcacagatg  10200

cgtaaggaga aaataccgca tcaggcgcca ttcgccattc aggctgcgca actgttggga  10260

agggcgatcg gtgcgggcct cttcgctatt acgccagctg gcgaaagggg gatgtgctgc  10320

aaggcgatta agttgggtaa cgccagggtt ttcccagtca cgacgttgta aaacgacggc  10380

cagtgcc                                                            10387
```

<210> SEQ ID NO 9
<211> LENGTH: 20
<212> TYPE: PRT
<213> ORGANISM: Porcine circovirus

<400> SEQUENCE: 9

```
Ser Tyr Pro Arg Arg Arg Tyr Arg Arg Arg Arg His His Pro Pro Ser
1               5                   10                  15

His Leu Gly Gln
            20
```

<210> SEQ ID NO 10
<211> LENGTH: 19
<212> TYPE: PRT
<213> ORGANISM: Porcine circovirus

<400> SEQUENCE: 10

```
Pro Arg His His Tyr Arg Pro Arg Arg Lys Asn Gly Ile Phe Asn Thr
1               5                   10                  15

Thr Leu Ser
```

<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

```
Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110
```

-continued

```
Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

PREVENTION AND TREATMENT OF SUB-CLINICAL PCVD

RELATED APPLICATIONS

This application is a continuation of U.S. patent application Ser. No. 13/079,498, filed Apr. 4, 2011, now patented as U.S. Pat. No. 8,496,940, which is a continuation of U.S. patent application Ser. No. 12/030,611 filed Feb. 13, 2008, now patented as U.S. Pat. No. 7,943,298, the teachings and content of which are hereby incorporated by reference.

SEQUENCE LISTING

This application contains a sequence listing in computer readable format, the teachings and content of which are hereby incorporated by reference. The sequence listing is identical with that found in European Patent Application No. EP 07102250.3 and in WO06/072065, the teaching and content both of which are hereby incorporated by reference.

BACKGROUND OF THE INVENTION

1. Field of the Invention

The present invention relates to the use of an immunogenic composition comprising a porcine circovirus type 2 (PCV2) antigen for the prevention and treatment of sub-clinical (chronic) PCV2 infections in animals, preferably in pigs.

2. Description of the Prior Art

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, infection of swine with PCV2 has recently been associated with a number of disease syndromes which have been collectively named Porcine Circovirus Diseases (PCVD) (also known as Porcine Circovirus associated Diseases (PCVAD)) (Allan et al, 2006, IPVS Congress). Postweaning Multisystemic Wasting Syndrome (PMWS) is generally regarded to be the major clinical manifestation of PCVD (Harding et al., 1997, Swine Health Prod; 5: 201-203; Kennedy et al., 2000, J Comp Pathol; 122: 9-24). Other potentially related conditions reported in the literature include porcine respiratory disease complex (PRDC), porcine dermatopathy and nephropathy syndrome (PDNS), reproductive failure, granulomatous enteritis, and potentially, congenital tremors (CT-A11) and perinatal myocarditis (Chae, Veterinary J., 2005; 169: 326-336).

PCVD affects pigs between 5-22 weeks of age. PCVD is clinically characterized by wasting, paleness of the skin, unthriftiness, respiratory distress, diarrhea, icterus, and jaundice. In some affected swine, a combination of all symptoms will be apparent while other affected swine will only have one or two of these symptoms (Muirhead, 2002, Vet. Rec.; 150: 456). The mortality rate for swine infected with PCV2 can approach 50%. During necropsy, microscopic and macroscopic lesions also appear on multiple tissues and organs, with lymphoid organs being the most common site for lesions (Allan and Ellis, 2000; J. Vet. Diagn. Invest., 12: 3-14). A strong correlation has been observed between the amount of PCV2 nucleic acid or antigen and the severity of microscopic lymphoid lesions (Brunborg, 2004). In addition, correlation has also been found for the amount of nucleic acid or antigen in blood and the severity of the clinical symptoms (Brunborg, 2004; Liu, 2000; Olvera, 2004). Pigs suffering from PCVD have been shown to have viral loads that are higher than $10^6$ genomic equivalents per ml.

In contrast to clinically apparent disease manifestations of PCV2 infection, sub-clinical PCV2 infections are thought to be present in those animals that are infected with PCV2 but are clinically asymptomatic. In general, a releationship exists between these forms of PCV2 infection since sub-clinical infections may easily transition into PCVD, and since convalescent animals may stay persistently (chronically) infected (see FIG. 1).

Recent observations have demonstrated that sub-clinical PCV2 infections are frequent events. The existence of sub-clinical infections has been demonstrated by both experimental and field studies. In laboratory studies it could be shown that PCV2 infection in individual pigs is not always associated with clinical signs or lesions (Harms et al., 2001, Vet. Pathol., 38:528-539). In addition, several field studies have shown that the incidence of PCV2 infected, seropositive herds is higher than the incidence of herds affected with PCVD (Olvera et al., 2004, J. Virol. Methods, 117: 75-80). Often, herds that have experienced an acute outbreak of PCVD remain PCV2 infected without showing any apparent clinical signs. According to the literature this form of sub-clinical (persistent) infection within a herd is also called "chronic" infection (Burch D., 2006, Pig International).

The economical impact of PCV2 in sub-clinically infected herds, if any, is unknown and has never been described so far. In particular, it was not known and no indication was ever given whether sub-clinical cases of PCV2 infections have any impact on growth performance of animals or, in general, on the overall health of the affected animals.

Approaches to treat PCV2 infections based on a DNA vaccine are described in U.S. Pat. No. 6,703,023. In WO 03/049703 production of a live chimeric vaccine is described, comprising a PCV1 backbone in which an immunogenic gene of a pathogenic PCV2 strain replaces a gene of the PCV-1 backbone. WO99/18214 has provided several PCV2 strains and procedures for the preparation of a killed PVC2 vaccine. However, no efficacy data have been reported. An effective ORF-2 based subunit vaccine has been reported in WO06/072065. Any of such vaccines are intended to be used for the vaccination/treatment of swine or pigs older than 3 weeks of age. None of these vaccines have ever been described for the prophylaxis or treatment of animals sub-clinically infected with PCV2. Moreover, such vaccines have not been described to confer immunity against PCV2 infection in sub-clinically infected groups of animals and/or to improve their growth performance.

DISCLOSURE OF THE INVENTION

Figure 1:
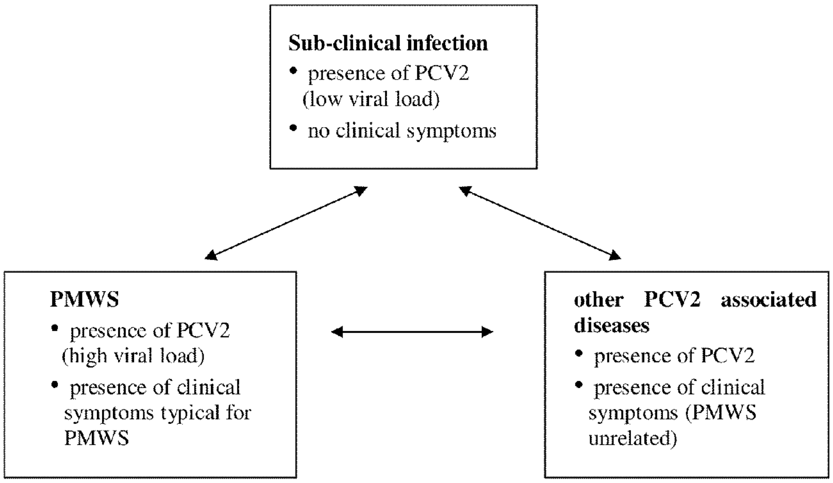
FIG. 1 is a schematic representation of the different forms of PCV2 infections and their relatedness.
Figure 2:
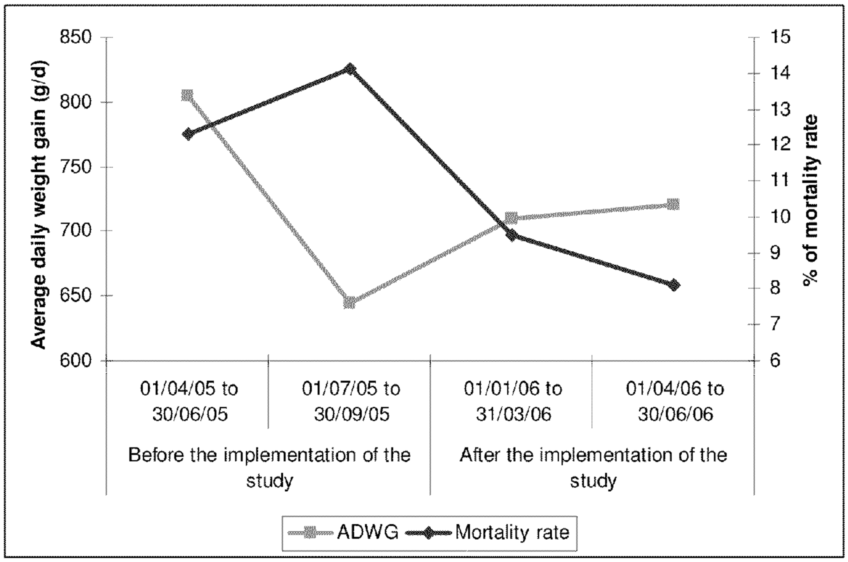
FIG. 2 is a graph of the mortality rate and average daily weight gain in fattening on the study farm before and after study initiation.

Clinically apparent PCV2 infections are associated with different disease syndromes. Depending on the PCV2-related disease expression form, clinical signs of an acute PCV2 infection may be one or more of the following findings: a) a significantly increased mortality rate (4-20% higher), b) a significant increase in the frequency of runts (5-50% more) and c) other clinically apparent signs such as respiratory symptoms, diarrhea, paleness of the skin, icterus, and unthriftiness (morbidity rate 4-60%). In addition, high viral titers of more than $10^6$ or $10^7$ per ml serum or tissue are a characteristic finding in most of the animals with acute signs of PCVD. Beside this acute PCV2 infection, sub-clinical PCV2 infections characterized by no or a low morbidity rate become more and more visible. In some cases, a situation of an acute PCV2 infection might shift into a sub-clinical PCV2 infection. However, sub-clinical infections may also occur without any previous sign of an acute PCV2 infection.

It has been surprisingly found that a sub-clinical PCV2 infection has a significant impact on performance parameters of apparently healthly pigs, and in particular the growth performance of pigs. Even if sub-clinically infected animals do not develop typical clinical symptoms which allow the identification of PCVD or do show only a low morbidity, those animals are significantly affected by the sub-clinical PCV2 infection. Sub-clinical infections of pigs with PCV2 result in a significant growth impairment including loss in weight gain (e.g. see example 3). As already mentioned, no evidence is given in the prior art so far that sub-clinical PCV2 infections have any impact on the health, and in particular on the growth performance of pigs.

Moreover, it has also been surpisingly found that growth impairment including reduction in weight gain caused by a sub-clinical PCV2 infection can be reduced by the treatment/vaccination of animals that become sub-clinically infected with PCV2 antigen (e.g. see example 3). Thus, it was not only found that the sub-clinical PCV2 infections affect the growth performance of pigs, evidence is also given that such a negative impact can be significantly reduced by treatment/vaccination of animals with PCV2 antigen. In other words, even if the phenomenon of sub-clinical infections have been described in the prior art, evidence is given now for the first time that

- the sub-clinical PCV2 infection, occasionally observed in the field, has a significant impact on the growth performance of pigs;
- vaccination of sub-clinically affected pigs or herds with PCV2 antigen can significantly reduce the negative impact of this sub-clinical PCV2 infection.

Therefore, according to one aspect, the present invention provides a method for the prophylaxis and treatment of a sub-clinical PCV2 infection in an animal or a group of animals, comprising the step of administering a therapeutically effective amount of PCV2 antigen or an immunogenic composition comprising a PCV2 antigen to an animal in need of such administration.

A "sub-clinical PCV2 infection" as used herein is characterized by i) a viral load in an individual animal that remains during the entire life below $10^6$ genomic copies of PCV2 per ml serum, ii) a low proportion of PCV2 positive animals within a group or herd with viral titers of more than $10^6$ genomic copies per ml serum, iii) a virus persistence in a group or herd of at least 6 weeks, preferably of at least 8 weeks, more preferably of at least 10 weeks, and most preferably of at least 12 weeks, iv) the absence of typical clinical symptoms in a PCV2 positive animal, v) no or only a low morbidity rate within a group of animals or herd of PCV2 positive animals and/or vi) a low mortality rate within a group of PCV2 positive animals or herd.

The term "low proportion of PCV2 positive animals" as used in criteria ii) above means that less than 20%, preferably less than 15%, even more preferably less than 10%, even more preferably less than 8%, even more preferably less than 6%, even more preferably less than 4%, and most preferably less than 3% of the PCV-2 positive animals within a group of animals or a herd have viral titers of more than $10^6$ genomic copies per ml serum. In other words, the term a "low proportion of PCV2 positive animals within a group or herd with viral titers of more than $10^6$ genomic copies per ml serum" also means, that more than 80%, preferably more than 85%, even more preferably more than 90%, even more preferably more than 92%, even more preferably more than 94%, even more preferably more than 96%, and most preferably more than 97% of the PCV2 positive animals of a group of animals or herd have viral titers of less than $10^6$ genomic copies of PCV2 per ml serum.

The term "PCV2 positive" as used herein means, but is not limited to, an animal that comprises a detectable amount of PCV2 genome equivalents (=viral copies) in a sample (1 ml serum or 1 mg tissue). A detectable amount of PCV2 genome equivalents means that PCV2 genome equivalents can be detected by a polymerase chain reaction (PCR) assay. A sample is considered PCR positive if two independent samples due to a positive PCR result in such assay.

Methods for quantification of PCV2 via a PCR assay are well known in the art. Actually, the quantification of PCV2 genome equivalents was/is done by the method described in Brunborg et al., 2004; J. Virol Methods 122: 171-178. For amplification of PCV2, primers PCV2-84-1265U21 and PCV2-84-1319L21 were/are used. Such methods shall function as reference assay in any case of doubt.

The term "virus persistence" as used herein means that the infected animal has a viral load of at least $10^4$ viral copies of PCV2 per ml serum for such period of time, i.e. for at least 6 weeks or longer as defined above.

The term "the absence of typical clinical symptoms in PCV2 positive animal", as used herein means the absence of any apparent clinical symptions normally associated with a clinically apparent PCV2 infection, that allow a precise and undoubtful identification of a PCV2 infection only by its typical clinical appearance. Such clinical symptoms are those known as PCVD, in particular paleness of the skin, unthriftiness, respiratory distress, diarrhea, icterus, or jaundice.

The term "low morbidity rate" as used herein is an indicator for the absence of clinical signs which allows the identification of an acute PCV2 infection by its clinical appearance. It is therefore an indicator for the existence of a sub-clinical PCV2 infection. The term "low morbidity rate" as used herein refers to the percentage of animals with altered general health. "Altered general health" as used herein is defined as the presence of one or more PCVD related clinical signs such as the occurrence of runts (defined herein as animals with a body weight 25% less than the mean weight of its animal group of the same age), paleness of the skin, unthriftiness, respiratory distress, diarrhea, icterus, or jaundice. Thus, a "low morbitidy" as used herein, means that less than 25%, preferably less than 20%, more preferably less than 15%, even more preferably less than 12%, even more preferably less than 10%, even more preferably less than 8%, even more preferably less than 6% and most preferably less than 4% of the animals of a group of animals or herd do show one or more clinical symptoms of PCVD, and more preferably do show the occurrence of runts as defined above, paleness of the skin, unthriftiness, respiratory distress, diarrhea, icterus, or jaundice.

The term "no morbidity rate" as used herein means, that less than 1% of the PCV2 positive animals of a group of animals or herd do show one or more clinical symptoms of PCVD, and more preferably do show the occurrence of runts as defined above, paleness of the skin, unthriftiness, respiratory distress, diarrhea, icterus, or jaundice.

The term "low mortality rate" as used herein means, but is not limited to, a mortality rate of less than 20%, preferably of less than 15%, more preferably of less than 12%, even more preferably of less than 10%, even more preferably of less than 8%, even more preferably of less than 6%, and most preferably of less than 4% of the PCV2 positive animals within a group of animals or a herd.

The term "in need of such administration" or "in need of such administration treatment", as used herein means that the administration/treatment is associated with prevention of health or any other positive medicinal effect on health of the aminals which receive the PCV2 antigen.

According to a preferred embodiment, a sub-clinical case of a PCV2 infection is given, when at least criteria i) "a viral load in an individual animal that remains during the entire life below $10^6$ genomic copies of PCV2 per ml serum", criteria ii) "a low proportion of PCV-2 positive animals within a group or herd with viral titers of more than $10^6$ genomic copies per ml serum" or criteria iii) "a virus persistence in a group or herd of at least 6 weeks, preferably of at least 8 weeks, more preferably of at least 10 weeks, and most preferably of at least 12 weeks" mentioned above are applicable. Most preferably a sub-clinical case of PCV2 infection is given, when criteria i) and ii) as mentioned above, are applicable.

In cases, where criteria i) and/or criteria ii) is combined with criteria iii) "a virus persistence in a group or herd of at least 6 weeks, preferably of at least 8 weeks, more preferably of at least 10 weeks, and most preferably of at least 12 weeks", or in any other cases comprising criteria iii) as defined above, the sub-clinical infection is considered to be a "chronic sub-clinical PCV2" infection.

According to a further aspect, the present invention provides a method for the prophylaxis and treatment of a sub-clinical PCV2 infection, wherein the sub-clinical PCV2 infection is characterized by a viral load in an individual animal of below $10^6$ genomic copies of PCV2 per ml serum, comprising the step of administering a therapeutically effective amount of PCV2 antigen or an immunogenic composition comprising a PCV2 antigen to that animal in need of such administration. Preferably, that sub-clinical PCV2 infection is further characterized by the presence of less than 20% of the animals with more than $10^6$ preferably more than $10^7$ viral copies of PCV2 per ml serum within a group of animals or a herd and/or a virus persistence in such group or herd of at least 6 weeks, preferably of at least 8 weeks, more preferably of at least 10 weeks, and most preferably of at least 12 weeks. More preferably, that sub-clinical infection is further characterized by the absence of any clinical signs in an individual PCV2 positive animal as defined above, no or a low morbidity rate as defined above, and/or a low mortality rate as defined above.

According to a further aspect, the present invention provides a method for the prophylaxis and treatment of sub-clinical PCV2 infection, wherein the sub-clinical PCV2 infection is characterized by a viral load in an individual animal that would remain during the entire life below $10^6$ genomic copies of PCV2 per ml serum in the absence of any PCV2 antigen administration, comprising the step of administering a therapeutically effective amount of PCV2 antigen or an immunogenic composition comprising a PCV2 antigen to that animal in need of such administration. Preferably, that sub-clinical PCV2 infection is further characterized by the presence of less than 20% of the animals with more than $10^6$ preferably more than $10^7$ viral copies of PCV2 per ml serum within a group of animals or a herd and/or a virus persistence in such group or herd of at least 6 weeks, preferably of at least 8 weeks, more preferably of at least 10 weeks, and most preferably of at least 12 weeks. More preferably, that sub-clinical infection is further characterized by the absence of any clinical signs in an individual PCV2 positive animal as defined above, no or a low morbidity rate as defined above, and/or a low mortality rate as defined above.

According to a further aspect, the present invention provides a method for the prophylaxis and treatment of sub-clinical PCV2 infection, wherein the sub-clinical PCV2 infection is characterized by the presence of less than 20% of the animals with more than $10^6$ preferably more than $10^7$ viral copies of PCV2 per ml serum within a group of animals or a herd, comprising the step of administering a therapeutically effective amount of PCV2 antigen or an immunogenic composition comprising a PCV2 antigen to that animal in need of such administration. Preferably, that sub-clinical PCV2 infection is further characterized by a virus persistence in such group or herd of at least 6 weeks, preferably of at least 8 weeks, more preferably of at least 10 weeks, and most preferably of at least 12 weeks. More preferably, that sub-clinical infection is further characterized by the absence of any clinical signs in an individual PCV2 positive animal as defined above, no or a low morbidity rate as defined above, and/or a low mortality rate as defined above.

According to a further aspect, the present invention provides a method for the prophylaxis and treatment of sub-clinical PCV2 infection, wherein the sub-clinical PCV2 infection is characterized by a virus persistence in a group of PCV2 positive animals or herd of at least 6 weeks, preferably of at least 8 weeks, more preferably of at least 10 weeks, and most preferably of at least 12 weeks. Preferably, that sub-clinical PCV2 infection is further characterized by the absence of any clinical signs in an individual PCV2 positive animal as defined above, no or a low morbidity rate as defined above, and/or a low mortality rate as defined above.

According to a further aspect, the present invention also provides a method for the prophylaxis and treatment of sub-clinical PCV2 infection, wherein the sub-clinical PCV2 infection is characterized by the absence of any clinical signs in an individual PCV2 positive animal as defined above, comprising the step of administering a therapeutically effective amount of PCV2 antigen or an immunogenic composition comprising a PCV2 antigen to an animal in need of such administration. Preferably, that sub-clinical PCV2 infection is further characterized by no or a low morbidity rate as defined above, and/or a low mortality rate as defined above. More preferably, such sub-clinical PCV2 infection is further characterized by a viral load in an individual animal that remains during the entire life below $10^6$ genomic copies of PCV2 per ml serum and/or a low proportion of PCV-2 positive animals within a group or herd with viral titers of more than $10^6$ genomic copies per ml serum.

According to a further aspect, the present invention also provides a method for the prophylaxis and treatment of sub-clinical PCV2 infection, wherein the sub-clinical PCV2 infection is characterized by no or low morbidity in a group of animals or a herd, preferably of less than 25% or lower as defined above, comprising the step of administering a therapeutically effective amount of PCV2 antigen or an immunogenic composition comprising a PCV2 antigen to an animal in need of such administration. Preferably, such sub-clinical PCV2 infection is further characterized by a viral load in an individual animal that remains during the entire life below $10^6$ genomic copies of PCV2 per ml serum and/or a low proportion of PCV2 positive animals within a group or herd with viral titers of more than $10^6$ genomic copies per ml serum.

According to a further aspect, the present invention also provides a method for the prophylaxis and treatment of sub-clinical PCV2 infection, wherein the sub-clinical PCV2 infection is characterized by low mortality rate as defined herein, preferably of less than 20% or lower, comprising the step of administering a therapeutically effective amount of PCV2 antigen or an immunogenic composition comprising a PCV2 antigen to an animal in need of such administration. Preferably, such sub-clinical PCV2 infection is further characterized by a viral load in an individual animal that remains during the entire life below $10^6$ genomic copies of PCV2 per ml serum and/or a low proportion of PCV2 positive animals within a group or herd with viral titers of more than $10^6$ genomic copies per ml serum.

The administration of an effective amount of PCV2 antigen to animals or a group of animals that are sub-clinically infected with PCV2 results in an enhanced weight gain of those animals in fattening, in reduction of the number of animals with viral load comprised between $10^4$ to $10^6$ genomic copies per ml serum, in reduction of virus nasal shedding, and/or in reduction of duration of viremia.

Thus according to a further aspect, the present invention also provides a method for reduction of loss of weight gain in animals sub-clinically infected with PCV2, comprising the step of administering a therapeutically effective amount of PCV2 antigen or an immunogenic composition comprising a PCV2 antigen to an animal in need of such administration. Preferably, average weight gain is increased in weeks 10 to 22 of age for more than 1.5 kg as compared to non vaccinated animals. The term "during fattening" as used herein means, but is not limited to, weeks 1 to 36 of age, preferably to weeks 10 to 28 of age of those animals.

The term "in animals sub-clinically infected with PCV2" as used herein means the individual animal that becomes sub-clinically infected with PCV2, but also refers to a group of animals wherein most of the animals of that group become sub-clinically infected with PCV2. Thus, the term "in animals sub-clinically infected with PCV2" has to be read as i) "in animals sub-clinically infected with PCV2" and ii) as "in animals of a herd, wherein said herd is sub-clinically infected with PCV2".

According to a further aspect, the present invention also provides a method for reduction of the number of animals with viral load comprising between $10^4$ to $10^6$ genomic copies per ml serum in a group of animals (herd) sub-clinically infected with PCV2, comprising the step of administering a therapeutically effective amount of PCV2 antigen or an immunogenic composition comprising a PCV2 antigen to an animal in need of such administration. Preferably, the number of animals with $10^4$ to $10^6$ genomic copies per ml serum could be reduced due to vaccination with PCV2 antigen to less than 30%, preferably less than 20%, even more preferably to less than 10%, and most preferably to less than 5%, whereas in the non-vaccinated control group of the sub-clinically infected animals (with viral load comprised between $10^4$ to $10^6$ genomic copies per ml serum) more than 40% developed PCV2 titers with $10^4$ to $10^6$ genomic copies per ml serum.

According to a further aspect, the present invention also provides a method for the reduction of the number of animals with a clinically relevant viral load (above $10^6$ genomic copies per ml serum) in a group of animals (herd) sub-clinically infected with PCV2, comprising the step of administering a therapeutically effective amount of PCV2 antigen or an immunogenic composition comprising an PCV2 antigen to an animal in need of such administration. Preferably, the number of animals with a viral load above $10^6$ genomic copies per ml serum could be reduced due to vaccination with PCV2 antigen to less than 10%, preferably less than 5%, even more preferably to less than 4%, even more preferably to less than 3%, even more preferably to less than 2%, and most preferably to less than 0.5%.

According to a further aspect, the present invention also provides a method for the reduction of nasal virus shedding, or reduction of the duration of viremia in animals sub-clinically infected with PCV2, comprising the step of administering a therapeutically effective amount of PCV2 antigen or an immunogenic composition comprising an PCV2 antigen to an animal in need of such administration. As described above, vaccination/treatment of animals sub-clinically infected with PCV2 resulted in shortening of viremic phase as compared to non-vaccinated control animals. The average shortening time of the duration of the viremia was 17 days as compared to non-vaccinated control animals of the same species. Thus, according to a further aspect, the present invention also provides a method for reduction of duration of viremia in animals sub-clinically infected with PCV2, comprising the step of administering a therapeutically effective amount of PCV2 antigen or an immunogenic composition comprising a PCV2 antigen to an animal in need of such administration, wherein the treatment or prophylaxis results in shortening of the viremia phase of 5 or more days, preferably 6 or more days, even more preferably of 7 or more days, even more preferably of 8 or more days, even more preferably of 9, even more preferably of 10, even more preferably of 12, even more preferably of 14, and most preferably of more than 16 days as compared to animals of a non-treated control group of the same species.

The term "antigen" as used herein refers to an amino acid sequence which elicits an immune response in a host. An antigen, as used herein, includes the full-length sequence of any PCV2 proteins, analogs thereof, or immunogenic fragments thereof. The term "immunogenic fragment" refers to a fragment of a protein which includes one or more epitopes and thus elicits the immune response in a host. Such fragments can be identified using any number of epitope mapping techniques well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

An "immune response" means, but is not limited to, the development in a host of a cellular and/or antibody-mediated immune response to an antigen, an immunogenic composition, or a vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with PCV2 infections, in delay of onset of viremia, in a reduced viral persistence, in a reduction of the overall viral load, and/or a reduction of viral excretion.

The terms "immunogenic composition" or "vaccine" (both terms are used synonymously) as used herein refers to any pharmaceutical composition containing a PCV2 antigen, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated, and/or inactivated PCV2.

Thus according to another aspect, the present invention provides a method for the prophylaxis and treatment of sub-clinical PCV2 infection, a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genome per ml serum within a sub-clinically infected herd, a method for the reduction of nasal virus shedding, a method for the reduction of duration of viremia in animals sub-clinically infected with PCV2, a method for the reduction of the morbidity rate within a sub-clinically infected herd, and a method for the reduction of the mortality rate within a sub-clinically infected herd, all comprising the step of administering a therapeutically effective amount of PCV2 antigen or an immunogenic composition comprising an PCV2 antigen to an animal in need of such treatment, wherein the immunogenic composition is a subunit immunogenic composition, and/or a composition containing whole killed, or attenuated, and/or inactivated PCV2.

The term "subunit immunogenic composition" as used herein refers to a composition containing at least one immunogenic polypeptide or antigen, but not all antigens, derived from or homologous to an antigen from PCV2. Such a composition is substantially free of intact PCV2. Thus, a "subunit immunogenic composition" is prepared from at least partially purified or fractionated (preferably substantially purified) immunogenic polypeptides from PCV2, or recombinant analogs thereof. A subunit immunogenic composition can comprise the subunit antigen or antigens of interest substantially free of other antigens or polypeptides from PCV2, or in fractionated form. A preferred immunogenic subunit composition comprises the PCV2ORF-2 protein as described below. Most preferred are immunogenic subunit compositions, which comprise any of the PCV2 antigens provided in WO06/072065, which are all incorporated herein by reference in their entirety.

According to a further aspect, the immunogenic composition as used herein most preferably comprises the polypeptide, or a fragment thereof, expressed by ORF-2 of PCV2. PCV2 ORF-2 DNA and protein, used herein for the preparation of the compositions and within the processes provided herein, is a highly conserved domain within PCV2 isolates and thereby, any PCV2ORF-2 would be effective as the source of the PCV2ORF-2 DNA and/or polypeptide as used herein. A preferred PCV2ORF-2 protein is that of SEQ ID NO: 11 of WO06/072065. A further preferred PCV ORF-2 polypeptide is provided as SEQ ID NO: 5 of WO06/072065. However, it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4 of WO06/072065. Moreover, the antigenic characteristic of a modified antigen is still retained, when the modified antigen confers at least 70%, preferably 80%, more preferably 90% of the protective immunity as compared to the PCV2ORF-2 protein, encoded by the polynucleotide sequence of SEQ ID NO:3 or SEQ ID NO:4 as provided in WO06/072065.

Thus according to another aspect, the present invention provides a method for the prophylaxis and treatment of sub-clinical PCV2 infection, a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genome per ml serum within a sub-clinically infected herd, a method for the reduction of nasal virus shedding, a method for the reduction of duration of viremia in animals sub-clinically infected with PCV2, a method for the reduction of the morbidity rate within a sub-clinically infected herd, and a method for the reduction of the mortality rate within a sub-clinically infected herd, all comprising the step of administering a therapeutically effective amount of PCV2 antigen or an immunogenic composition comprising a PCV2 antigen to an animal in need of such administration, wherein the PCV2 antigen is an antigen such as PCV2ORF-2 protein that has at least 70%, preferably 80%, even more preferably 90% of the protective immunity as compared to the PCV2ORF-2 protein, encoded by the polynucleotide sequence of SEQ ID NO:3 or SEQ ID NO:4 as provided in WO06/072065. Preferably said PCV2ORF-2 has the sequence of SEQ ID NO: 11 or SEQ ID NO: 5 of WO06/072065.

In some forms, immunogenic portions of PCV2ORF-2 protein are used as the antigenic component in the immunogenic composition, comprising PCV2 antigen. The term "immunogenic portion" as used herein refers to truncated and/or substituted forms, or fragments of PCV2ORF-2 protein and/or polynucleotide, respectively. Preferably, such truncated and/or substituted forms or fragments will comprise at least 6 contiguous amino acids from the full-length ORF-2 polypeptide. More preferably, the truncated or substituted forms or fragments will have at least 5, preferably at least 8, more preferably at least 10, more preferably at least 15, and still more preferably at least 19 contiguous amino acids from the full-length PCV ORF-2 polypeptide. Two preferred sequences in this respect are provided as SEQ ID NO: 9 and SEQ ID NO: 10 of WO06/072065. It is further understood that such sequences may be a part of larger fragments or truncated forms.

As mentioned above, a further preferred PCV2ORF-2 polypeptide is any one encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form or fragment of this PVC2ORF-2 polypeptide is used as the antigenic component in the composition. Preferably, such truncated or substituted forms or fragments will comprise at least 18 contiguous nucleotides from the full-length PCV2ORF-2 nucleotide sequence, e.g. of SEQ ID NO: 3 or SEQ ID NO: 4. More preferably, the truncated or substituted forms or fragments, will have at least 30, more preferably at least 45, and still more preferably at least 57 contiguous nucleotides of the full-length PCV2ORF-2 nucleotide sequence, e.g. SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990)), the teachings of which are incorporated herein by reference. These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus according to another aspect, the present invention provides a method for the prophylaxis and treatment of sub-clinical PCV2 infection, a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genome per ml serum within a sub-clinically infected herd, a method for the reduction of nasal virus shedding, a method for the reduction of duration of viremia in animals sub-clinically infected with PCV2, a method for the reduction of the morbidity rate within a sub-clinically infected herd, and a method for the reduction of the mortality rate within a sub-clinically infected herd, all comprising the step of administering a therapeutically effective amount of PCV20RF-2 protein to an animal in need of such administration, wherein said PCV20RF-2 protein is any one of those described above. Preferably, said PCV20RF-2 protein is i) a polypeptide comprising the sequence of SEQ ID NO: 5, SEQ ID NO: 6, SEQ ID NO: 9, SEQ ID NO: 10 or SEQ ID NO: 11 of WO06/07065;
ii) any polypeptide that is at least 80% homologous to the polypeptide of i),
iii) any immunogenic portion of the polypeptides of i) and/or ii)
iv) the immunogenic portion of 11i), comprising at least 5, preferably at least 8, even more preferably at least 10 contiguous amino acids included in the sequences of SEQ ID NO: 5, SEQ ID NO: 6, SEQ ID NO: 9, SEQ ID NO: 10 or SEQ ID NO: 11 of WO06/072065,
v) a polypeptide that is encoded by a DNA comprising the sequence of SEQ ID NO: 3 or SEQ ID NO: 4 of WO06/072065.
vi) any polypeptide that is encoded by a polynucleotide that is at least 80% homologous to the polynucleotide of v),
vii) any immunogenic portion of the polypeptides encoded by the polynucleotide of v) and/or vi)
viii) the immunogenic portion of vii), wherein the polynucleotide coding for said immunogenic portion comprises at least 30 contiguous nucleotides included in the sequences of SEQ ID NO: 3, or SEQ ID NO: 4 of WO06/072065.

Preferably any of those immunogenic portions have the immunogenic characteristics of PCV20RF-2 protein that is encoded by the sequence of SEQ ID NO: 3 or SEQ ID NO: 4 of WO06/07065.

According to a further aspect, PCV20RF-2 protein is provided in the immunogenic composition at an antigen inclusion level effective for the treatment of animals sub-clinically infected with PCV2. Preferably, the PCV20RF-2 protein inclusion level is at least 0.2 μg antigen/ml of the final immunogenic composition (μg/ml), more preferably from about 0.2 to about 400 μg/ml, still more preferably from about 0.3 to about 200 μg/ml, even more preferably from about 0.35 to about 100 μg/ml, still more preferably from about 0.4 to about 50 μg/ml, still more preferably from about 0.45 to about 30 μg/ml, still more preferably from about 0.6 to about 15 μg/ml, even more preferably from about 0.75 to about 8 μg/ml, even more preferably from about 1.0 to about 6 μg/ml, still more preferably from about 1.3 to about 3.0 μg/ml, even more preferably from about 1.4 to about 2.5 μg/ml, even more preferably from about 1.5 to about 2.0 μg/ml, and most preferably about 1.6 μg/ml.

According to a further aspect, the PCV ORF-2 antigen inclusion level is at least 0.2 μg/PCV2 ORF-2 protein as described above per dose of the final antigenic composition (μg/dose), more preferably from about 0.2 to about 400 μg/dose, still more preferably from about 0.3 to about 200 μg/dose, even more preferably from about 0.35 to about 100 μg/dose, still more preferably from about 0.4 to about 50 μg/dose, still more preferably from about 0.45 to about 30 μg/dose, still more preferably from about 0.6 to about 15 μg/dose, even more preferably from about 0.75 to about 8 μg/dose, even more preferably from about 1.0 to about 6 μg/dose, still more preferably from about 1.3 to about 3.0 μg/dose, even more preferably from about 1.4 to about 2.5 μg/dose, even more preferably from about 1.5 to about 2.0 μg/dose, and most preferably about 1.6 μg/dose.

The PCV20RF-2 polypeptide used in the immunogenic composition in accordance with the present invention can be derived in any fashion including isolation and purification of PCV2 ORF2, standard protein synthesis, and recombinant methodology. Preferred methods for obtaining PCV20RF-2 polypeptide are provided in WO06/072065, the teachings and content of which are hereby incorporated by reference in its entirety. Briefly, susceptible cells are infected with a recombinant viral vector containing PCV20RF-2 DNA coding sequences, PCV20RF-2 polypeptide is expressed by the recombinant virus, and the expressed PCV20RF-2 polypeptide is recovered from the supernatant by filtration and inactivated by any conventional method, preferably using binary ethylenimine, which is then neutralized to stop the inactivation process.

The immunogenic composition as used herein also refers to a composition that comprises i) any of the PCV20RF-2 proteins described above, preferably in concentrations described above, and ii) at least a portion of the viral vector expressing said PCV20RF-2 protein, preferably of a recombinant baculovirus. Moreover, the immunogenic composition can comprise i) any of the PCV20RF-2 proteins described above, preferably in concentrations described above, ii) at least a portion of the viral vector expressing said PCV20RF-2 protein, preferably of a recombinant baculovirus, and iii) a portion of the cell culture supernatant.

Thus according to another aspect, the present invention provides a method for the prophylaxis and treatment of sub-clinical PCV2 infection, a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genome per ml serum within a sub-clinically infected herd, a method for the reduction of nasal virus shedding, a method for the reduction of duration of viremia in animals sub-clinically infected with PCV2, a method for the reduction of the morbidity rate within a sub-clinically infected herd, and a method for the reduction of the mortality rate within a sub-clinically infected herd, all comprising the step of administering a therapeutically effective amount of PCV2 antigen or an immunogenic composition comprising an PCV2 antigen to an animal in need of such treatment, wherein the PCV2 antigen is recombinant PCV20RF-2, preferably a baculovirus expressed PCV20RF-2, most preferably those recombinant or baculovirus expressed PCV20RF-2 having the sequence as described above.

The immunogenic composition as used herein also refers to a composition that comprises i) any of the PCV20RF-2 proteins described above, preferably in concentrations described above, ii) at least a portion of the viral vector expressing said PCV20RF-2 protein, preferably of a recombinant baculovirus, and iii) a portion of the cell culture; wherein about 90% of the components have a size smaller than 1 μm.

The immunogenic composition as used herein also refers to a composition that comprises i) any of the PCV20RF-2 proteins described above, preferably in concentrations described above, ii) at least a portion of the viral vector expressing said PCV20RF-2 protein, iii) a portion of the cell culture, iv) and an inactivating agent to inactivate the recombinant viral vector, preferably BEI, wherein about 90% of the components i) to iii) have a size smaller than 1 μm. Preferably, BEI is present in concentrations effective to inactivate the baculovirus, preferably in an amount of 2 to about 8 mM BEI, and more preferably of about 5 mM BEI.

The immunogenic composition as used herein also refers to a composition that comprises i) any of the PCV20RF-2 proteins described above, preferably in concentrations described above, ii) at least a portion of the viral vector expressing said PCV20RF-2 protein, iii) a portion of the cell culture, iv) an inactivating agent to inactivate the recombinant viral vector, preferably BEI, and v) a neutralization agent to stop the inactivation mediated by the inactivating agent, wherein about 90% of the components i) to iii) have a size smaller than 1 μm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV20RF-2 protein as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions, are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminium hydroxide and aluminium phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 μg to about 5 mg per dose, even more preferred in an amount of about 750 μg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 μg to about 5 mg per dose. Even more preferably, the adjuvant is added in an amount of about 750 μg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith contains PCV20RF-2 protein recovered from the supernatant of in vitro cultured cells, wherein said cells were infected with a recombinant viral vector containing PCV20RF-2 DNA and expressing PCV20RF-2 protein, and wherein said cell culture was treated with about 2 to about 8 mM BEI, and more preferably with about 5 mM BEI to inactivate the viral vector, and an equivalent concentration of a neutralization agent, preferably sodium thiosulfate solution, to a final concentration of about 2 to about 8 mM, and more preferably of about 5 mM.

The present invention also relates to the use of an immunogenic composition for increasing average weight gain in an animal or a group of animals (herd) sub-clinically infected with PCV2, the reduction of the number of animals with viral load comprised between $10^4$ to $10^6$ genomic copies per ml serum, the reduction of the number of animals with viral load above $10^6$ genome per ml serum within a sub-clinically infected herd, the reduction of nasal virus shedding, reduction of duration of viremia in animals sub-clinically infected with PCV2, a reduction of the morbidity rate within a sub-clinically infected herd, a method for the reduction of the mortality rate within a sub-clinically infected herd, wherein said immunogenic composition comprises i) any of the PCV20RF-2 proteins described above, preferably in concentrations described above, ii) at least a portion of the viral vector expressing said PCV20RF-2 protein, iii) a portion of the cell culture, iv) an inactivating agent to inactivate the recombinant viral vector, preferably BEI, and v) a neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to iii) have a size smaller than 1 μm.

According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml i) at least 1.6 μg of PCV20RF-2 protein described above, ii) at least a portion of baculovirus expressing said PCV20RF-2 protein iii) a portion of the cell culture, iv) about 2 to 8 mM BEI, v) sodium thiosulfate in equivalent amounts to BEI, vi) about 1 mg Carbopol 971, and vii) phosphate salt in a physiologically acceptable concentration; wherein about 90% of the components i) to iii) have a size smaller than 1 μm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 μg to about 2000 μg of adjuvant and preferably about 250 μg/ml dose of the vaccine composition. Thus, the immunogenic composition as used herein also refers to a composition that comprises from about 1 ug/ml to about 60 μg/ml of antibiotics, and more preferably less than about 30 μg/ml of antibiotics.

The immunogenic composition as used herein also refers to a composition that comprises i) any of the PCV20RF-2 proteins described above, preferably in concentrations described above, ii) at least a portion of the viral vector expressing said PCV20RF-2 protein, iii) a portion of the cell culture, iv) an inactivating agent to inactivate the recombinant viral vector, preferably BEI, v) a neutralization agent to stop the inactivation mediated by the inactivating agent, preferably sodium thiosulfate in equivalent amounts to BEI, vi) a suitable adjuvant, preferably Carbopol 971 in amounts described above, vii) a pharmaceutical acceptable concentration of a saline buffer, preferably of a phosphate salt, and viii) an anti-microbiological active agent; wherein about 90% of the components i) to iii) have a size smaller than 1 μm.

The immunogenic composition as used herein also refers to Ingelvac® CircoFLEX™ (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA). Thus according to another aspect, the present invention provides a method for the prophylaxis and treatment of sub-clinical PCV2 infection, a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genomic copies per ml serum within a sub-clinically infected herd, a method for the reduction of nasal virus shedding, a method for the reduction of the duration of viremia in animals sub-clinically infected with PCV2, a method for the reduction of the morbidity rate wtihin a sub-clinically infected herd, and a method for the reduction of the mortality rate within a sub-clinically infected herd, comprising the step of administering an effective amount of PCV2 antigen to an animal in need of such administration, wherein said immunogenic composition comprising a PCV2 antigen is Ingelvac® CircoFLEX™, CircoVac®, CircoVent and/or Suvaxyn PCV-2 One Dose®, and preferably it is Ingelvac® CircoFLEX™.

The term "an effective amount of PCV2 antigen" as used herein means, but is not limited to, an amount of PCV2 antigen that elicits or is able to elicit an immune response in an animal, to which said effective amount of PCV2 antigen is administered.

The amount that is effective depends on the ingredients of the vaccine and the schedule of administration. Typically, when an inactivated virus or a modified live virus preparation is used in the vaccine, an amount of the vaccine containing about $10^{2.0}$ to about $10^{9.0}$ $TCID_{50}$ per dose, preferably about $10^{3.0}$ to about $10^{8.0}$ $TCID_{50}$ per dose, and more preferably about $10^{4.0}$ to about $10^{8.0}$ $TCID_{50}$ per dose is used. In particular, when modified live PCV2 is used in the vaccines, the recommended dose to be administered to the susceptible animal is preferably about $10^{3.0}$ $TCID_{50}$ (tissue culture infective dose 50% end point)/dose to about $10^{6.0}$ $TCID_{50}$/dose and more preferably about $10^{4.0}$ $TCID_{50}$/dose to about $10^{5.0}$ $TCID_{50}$/dose. In general, the quantity of antigen will be between 0.2 and 5000 micrograms, and between $10^{2.0}$ and $10^{9.0}$ $TCID_{50}$, preferably between $10^{3.0}$ and $10^{6.0}$ $TCID_{50}$, and more preferably between $10^{4.0}$ and $10^{5.0}$ $TCID_{50}$, when purified antigen is used.

Sub-unit vaccines are normally administered with an antigen inclusion level of at least 0.2 μg antigen per dose, preferably with about 0.2 to about 400 μg/dose, still more preferably with about 0.3 to about 200 μg/dose, even more preferably with about 0.35 to about 100 μg/dose, still more preferably with about 0.4 to about 50 μg/dose, still more preferably with about 0.45 to about 30 μg/dose, still more preferably with about 0.6 to about 16 μg/dose, even more preferably with about 0.75 to about 8 μg/dose, even more preferably with about 1.0 to about 6 μg/dose, and still more preferably with about 1.3 to about 3.0 μg/dose.

Maternally derived immunity has been shown to confer a certain degree of protection against PCV2 infection and clinical diseases associated with PCV2 infections. This protection has been shown to be titer dependent: higher titers are generally protective whereas lower titers are not (McKeown et al., 2005; Clin. Diagn. Lab. Immunol.; 12: 1347-1351). The mean antibody half-life in weanlings has been estimated to be 19.0 days and the window for PCV2-passive antibody decay within a population is relatively wide (Opriessnig et al. 2004, J. Swine Health Prod. 12:186-191). The presence of maternally derived antibody not only may confer a certain degree of protection against viral infections, which however is not predictable, but is also known to impair the efficacy of immunization. It has been surprisingly found that the presence of anti-PCV2 antibodies, in particular of anti-PCV2 antibody titers of up to 1:1000, does not affect the efficacy of the PCV2 treatment.

Thus according to another aspect, the present invention provides a method for the prophylaxis and treatment of subclinical PCV2 infection, a method for increasing average weight gain in an animal or a group of animals (herd) subclinically infected with PCV2, a method for the reduction of the number of animals with viral load comprised between $10^4$ to $10^6$ genomic copies per ml serum, a method for reduction of the number of animals with viral load above $10^6$ genomic copies per ml serum within a sub-clinically infected herd, a method for the reduction of nasal virus shedding, a method for the reduction of the duration of viremia in animals subclinically infected with PCV2, a method for the reduction of the morbidity rate within a sub-clinically infected herd, and a method for the reduction of the mortality rate within a subclinically infected herd all comprising the step of administering a therapeutically effective amount of PCV2 antigen or an immunogenic composition comprising a PCV2 antigen to an animal in need of such administration, wherein the animals at the time of vaccination have anti-PCV2 antibodies, preferably wherein said animals have at the time of vaccination a detectable anti-PCV2 antibody titer of up to 1:100, preferably of more than 1:100, even more preferably of more than 1:250, even more preferably of more than 1:500, even more preferably of 1:640; even more preferably of more than 1:750, and most preferably of more than 1:1000. Preferably, the anti-PCV2 antibody titer is detectable and quantifiable in a specific anti-PCV2 immune assay, preferably in the assay as described in Example 2.

Methods for the detection and quantification of anti-PCV2 antibodies are well known in the art. For example, the detection and quantification of PCV2 antibodies can be performed by indirect immunofluorescence as described in Magar et al., 2000, Can. J. Vet Res.; 64: 184-186 or Magar et al., 2000, J. Comp. Pathol.; 123: 258-269. Further assays for quantification of anti-PCV2 antibodies are described in Opriessnig et al., 2006, $37^{th}$ Annual Meeting of the American Association of Swine Veterinarians. Moreover, Example 2 also describes an indirect immunofluorescence assay, which can be used by a person skilled in the art. In cases of controversial results and in any question of doubt, anti-PCV2 titers as mentioned herein refer to those which are/can be estimated by the assay as described in Example 2.

Thus according to another aspect, the present invention provides a method for the prophylaxis and treatment of subclinical PCV2 infection, a method for increasing average weight gain in an animal or a group of animals (herd) subclinically infected with PCV2, a method for the reduction of the number of animals with viral load comprised between $10^4$ to $10^6$ genomic copies per ml serum, a method for the reduction of the number of animals with viral load above $10^6$ genomic copies per ml serum within a sub-clinically infected herd, a method for the reduction of nasal virus shedding, a method for the reduction of duration of viremia in animals sub-clinically infected with PCV2, a method for the reduction of the morbidity rate within a sub-clinically infected herd, and a method for the reduction of the mortality rate within a sub-clinically infected herd, all comprising the step of administering a therapeutically effective amount of PCV2 antigen or an immunogenic composition comprising a PCV2 antigen to a young animal in need of such administration.

The term "young animal" as used herein refers to an animal of 1 to 22 days of age. Preferably, by the term young animal, an animal of 1 to 20 days of age is meant. More preferably, the term young animal refers to an animal of 1 to 15 days of age, even more preferably of 1 day of age to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, and most preferably to an animal of 1 day of age.

Due to the ubiquity of PCV2 in the field, most of the young piglets are seropositve in respect to PCV2. Thus according to a further aspect, said young animals, at the day of vaccination/treatment, have a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000 at the day of vaccination/treatment.

The composition according to the invention may be applied intradermally, intratracheally, or intravaginally. The composition preferably may be applied intramuscularly or intranasally, most preferably intramuscularly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

Preferably, at least one dose of the immunogenic composition as described above is intramuscularly administered to the subject in need thereof. According to a further aspect, the PCV2 antigen or the immunogenic composition comprising any such PCV2 antigen as described herein is bottled in and administered at one (1) ml to five (5) ml per dose, preferably to 1 ml per dose. Thus, according to a further aspect, the present invention also provides a 1 ml to 5 ml, preferably a 1 ml immunogenic composition, comprising PCV-2 antigen as described herein, for the prophylaxis and treatment of sub-clinical PCV2 infection in an animal or group of animals (herds), for increasing average weight gain in an animal or a group of animals (herd) sub-clinically infected with PCV2, the reduction of the number of animals with viral load comprised between $10^4$ to $10^6$ genomic copies per ml serum, the reduction of the number of animals with viral load above $10^6$ genomic copies per ml serum within a sub-clinically infected herd, the reduction of nasal virus shedding and reduction of duration of viremia in animals sub-clinically infected with PCV2, a method for the reduction of morbidity rate within a sub-clinically infected herd, and a method for the reduction of the mortality rate within a sub-clinically infected herd all comprising the step of administering a therapeutically effective amount of PCV2 antigen or an immunogenic composition comprising a PCV2 antigen to an animal in need of such administration. The present invention also relates to a method for the prophylaxis and treatment of sub-clinical PCV2 infection in an animal or group of animals (herds), a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genomic copies per ml serum within a sub-clinically infected herd, a method for the reduction of nasal virus shedding, a method for the reduction of the duration of viremia in animals sub-clinically infected with PCV2, a method for the reduction of the morbidity rate within a sub-clinically infected herd, and a method for the reduction of the mortality rate within a sub-clinically infected herd, all comprising the step of administering 1 to 5 ml, preferably 1 ml of a therapeutically effective amount of PCV2 antigen or an immunogenic composition comprising an PCV2 antigen to an animal in need of such administration.

According to a further aspect, at least one further administration of at least one dose of the immunogenic composition as described above is given to a subject in need thereof, wherein the second or any further administration is given at least 14 days beyond the initial or any former administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant. Preferably, the immune stimulant is given at least 10 days, preferably 15 days, even more preferably 20 days, and even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

The present invention also relates to the use of a PCV2 antigen or an immunogenic composition comprising PCV2 antigen for the preparation of a medicine for the prophylaxis and treatment of chronic PCV2 infection in an animal or group of animals (herds), for increasing average weight gain in an animal or a group of animals (herd) sub-clinically infected with PCV2, the reduction of the number of animals with viral load comprised between $10^4$ to $10^6$ genomic copies per ml serum, the reduction of the number of animals with viral load above $10^6$ genomic copies per ml serum within a sub-clinically infected herd, the reduction of nasal virus shedding and the reduction of the duration of viremia in animals sub-clinically infected with PCV2, method for the reduction of the morbidity rate within a sub-clinically infected herd, and a method for the reduction of the mortality rate within a sub-clinically infected herd. Preferably, the PCV2 antigen is a recombinant antigen, preferably PCV2ORF-2, even more preferably Ingelvac® CircoFLEX™.

The "animal" as used herein means swine, pig or piglet. Thus according to another aspect, the present invention provides a method for the prophylaxis and treatment of sub-clinical PCV2 infection in pigs, a method for increasing average weight gain in an animal or a group of animals (herd) sub-clinically infected with PCV2, a method for the reduction of the number of animals with viral load comprised between $10^4$ to $10^6$ genomic copies per ml serum, a method for the reduction of the number of animals with viral load above $10^6$ genomic copies per ml serum within a sub-clinically infected herd, a method for the reduction of nasal virus shedding, a method for the reduction of the duration of viremia in animals sub-clinically infected with PCV2, a method for the reduction of the morbidity rate within a sub-clinically infected herd, and a method for the reduction of the mortality rate within a sub-clinically infected herd, all comprising the step of administering a therapeutically effective amount of PCV2 antigen or an immunogenic composition comprising a PCV2 antigen to pigs in need of such administration. Preferably, the PCV2 antigen or immunogenic composition comprising PCV2 antigen is anyone of those described supra, most preferably the PCV2 antigen is Ingelvac® CircoFLEX™.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

EXAMPLE 1

Preparation of PCV2ORF-2 Antigen

Initial SF+ cell cultures from liquid nitrogen storage were grown in Excell 420 media (JRH Biosciences, Inc., Lenexa, Kans.) in suspension in sterile spinner flasks with constant agitation. The cultures were grown in 100 mL to 250 mL spinner flasks with 25 to 150 mL of Excell 420 serum-free media. When the cells had multiplied to a cell density of $1.0–8.0\times10^6$ cells/mL, they were split to new vessels with a planting density of $0.5–1.5\times10^6$ cells/mL. Subsequent expansion cultures were grown in spinner flasks up to 36 liters in size or in stainless steel bioreactors of up to 300 liters for a period of 2-7 days at 25-29° C.

After seeding, the flasks were incubated at 27° C. for four hours. Subsequently, each flask was seeded with a recombinant baculovirus containing the PCV20RF-2 gene (SEQ ID NO: 4). The recombinant baculovirus containing the PCV20RF-2 gene was generated as described in WO06/072065. After being seeded with the baculovirus, the flasks were then incubated at 27±2° C. for 7 days and were also agitated at 100 rpm during that time. The flasks used ventilated caps to allow for air flow.

After incubation, the resulting supernatant was harvested, filtered in order to remove cell debris, and inactivated. The supernatant was inactivated by bringing its temperature to 37±2° C. and binary ethlylenimine (BEI) was added to the supernatant to a final concentration of 5 mM. The samples were then stirred continuously for 72 to 96 hrs. A 1.0 M sodium thiosulfate solution to give a final minimum concentration of 5 mM was added to neutralize any residual BEI. After inactivation, PCV20RF-2 buffered with phosphate buffer and Carbopol was added to about 0.5 to 2.5 mg/dose. The final dose comprises about 16 μg PCV2 ORF-2 antigen.

EXAMPLE 2

Anti PCV-2 Immuno Assay

PK15 (e.g. ATCC CCL-33) or VIDO R1 cells described in WO 02/07721, are seeded onto a 96 well plate (about 20.000 to 60.000 cells per wells). Cells are infected with a PCV2 isolate, when monolayers are approximately 65 to 85% confluent. Infected cells are incubated for 48 hours. Medium is removed and wells are washed 2 times with PBS. The wash buffer is discarded and cells are treated with cold 50/50 methanol/acetone fixative (~100 μl/well) for about 15 mM at about −20° C. The fixative is discarded and the plates are air tried. Serial dilutions of porcine serum samples are prepared in PBS, added to the plates and incubated to allow antibodies to bind if present in the serum samples for about 1 hr at 36.5±1° C. In addition, serial dilutions of an anti-PCV2 positive and negative control sample (Positive Control and Negative Control Samples) are run in parallel. The plates are then washed three times with PBS. The PBS is discarded. Plates are then stained with a commercial Goat anti-Swine FITC conjugate diluted 1:100 in PBS and incubated for about 1 hr at 36.5±1° C., which allows detection of antibodies bound to infected cells. After incubation is complete, the microplates are removed from the incubator, the conjugate is discarded and the plates are washed 2 times with PBS. The plates were read using UV microscopy and individual wells reported as positive or negative. The Positive Control and Negative Control samples are used to monitor the test system. If the controls are within expected ranges the test results are acceptable in regard to test method parameters. The serum antibody titers were calculated using the highest dilution showing specific IFA reactivity and the number of wells positive per dilution, or a 50% endpoint is calculated using the appropriate Reed-Muench formula.

EXAMPLE 3

Efficacy of PCV20RF-2 (Ingelvac® CircoFLEX™) in Treatment of Chronic PCV2 Infection Study Objective and Design Conventional piglets from five consecutive week groups, each comprising approximately 300 animals were included into this study Animals were equally distributed among two treatment groups with respect to initial body weight and litter assignment. At the day of weaning, one group (n=775) was vaccinated with Ingelvac® CircoFLEX, containing the minimum release antigen content and the other group of piglets (n=773) received control product (physiological saline). The vaccine and the control product (CP) were given as a single 1 ml dose intramuscularly in the right neck region when piglets were approx. 21 days old. Individual live body weights of all study animals were collected. Clinical observations with respect to PCV2 associated symptoms were performed and deviations from normal general health were recorded on an individual animal basis.

Serum samples and nasal secretions were analyzed quantitatively by Polymerase Chain Reaction (PCR) for the presence of PCV2. In addition, the PCV2 antibody titers from all study animals at the time of vaccination and from the same 5% of the pre-selected study animals were analyzed by an Indirect Fluorescent Antibody Titration (IFAT) test as described in Exampe 2.

Confirmation of the Chronic (Sub-Clinical) Status of the Study Site:

The first diagnosis of PCVD on the farm was done 4 months before the performance of the study. A mortality rate of 14.1% and the presence of runts in the fattening unit were identified. The growth performance was rather low (644 g/d). The presence of a PCV2 infection was confirmed by histological examination. The lung sample showed interstitial pneumonia and PCV-2 was identified by IHC among the lesions.

When looking at FIG. 1, it can be seen that the mortality rate in fattening decreased considerably from 14.1% to 8.1% suggesting a shift of an acute PCVD infection to sub-clinical infection.

Confirmation of the Subclinical Infection of the Study Animals

The shift to sub-clinical infection on the farm was confirmed by the results obtained during the study. The study animals were characterized by a predominant sub-clinical viral load, a low mortality rate (below 10%) and a low morbidity rate (below 10%).

Results

Viremia

Figure 4:
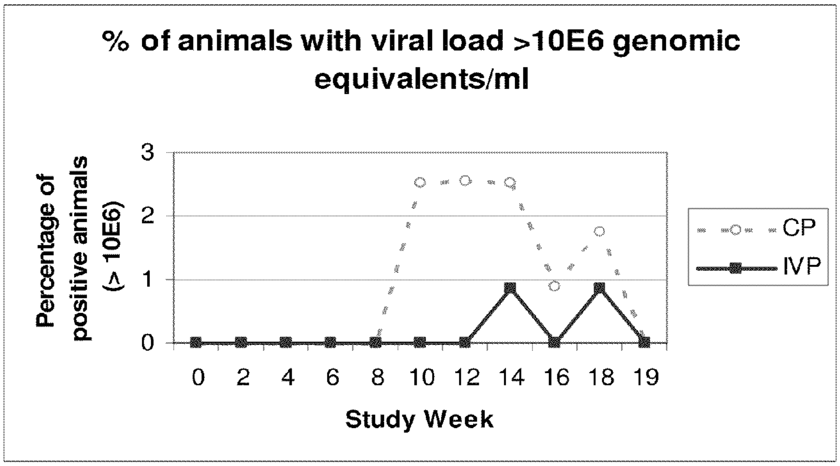
FIG. 4 is a graph illustrating a comparison of the percentage of animals with a virus load of $>10^6$ genomic equivalents/ml of serum in both treatment groups.
Figure 5:
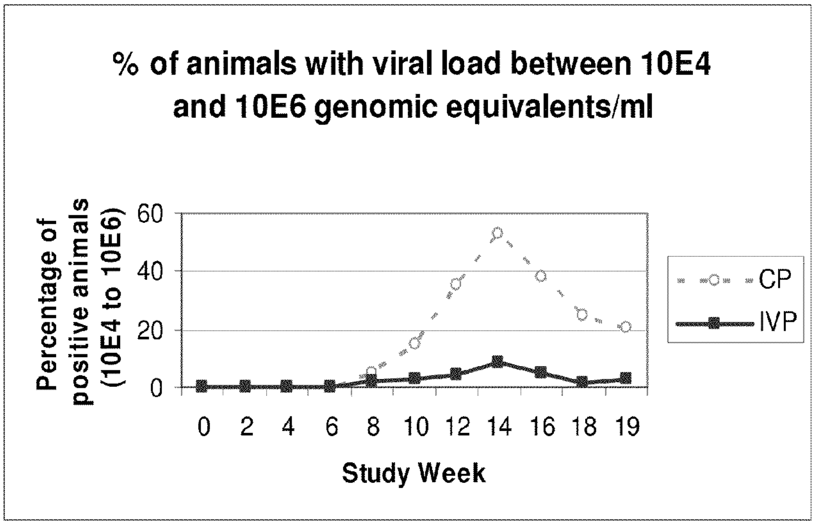
FIG. 5 is a graph illustrating a comparison of the percentage of animals with a virus load of $10^4$-$10E^6$ genomic equivalents/ml of serum in both treatment groups.

The highest proportion of viremic animals was observed at study week 14 with 55.5% viremic animals in the CP-treated group and approximately 10% viremic animals in the vaccinated group. As shown in FIGS. 4 and 5, the majority of animals in both treatment groups had only sub-clinical viral loads (defined as $10^4$-$10^6$ genomic equivalents per ml). The highest proportion of animals with clinically relevant PCV2 loads (>$10^6$ genomic equivalents per ml) was 2.52% for CP-treated animals and 0.87% for vaccinated animals.

Mortality

The mortality rate before and after onset of viremia was rather low. Prior to the onset of viremia, the mortality rate was 1.55% in the vaccinated animals and 2.19% in the CP-treated animals. After the onset of viremia an increase in the mortality rate was observed in CP-treated animals (from 1.55% to 3.02%) whereas the mortality rate in vaccinated animals was slightly decreased compared to the time before onset of viremia (from 2.19% to 1.98%). The differences in the mortality rate among both treatment groups before and after onset of viremia did not reach statistical significance.

Clinical Signs

Before onset of viremia only few clinical signs were detected in both treatment groups with incidences below 1% for each of the analyzed parameters. The onset of viremia was accompanied by a co-infection with PRRSV and *Mycoplasma hyopneumoniae*. However, neither PCV2 nor any other co-infectious pathogen caused severe clinical signs. Accordingly, the proportion of animals with respiratory symptoms such as cough and/or dyspnea was only 3.9% and 0.7% in the CP-treated group and 3.0% and 0.4% in the vaccinated group. The frequency of other clinical findings was always below 1% and not different between treatment groups.

Frequency of Runts

No significant differences in the frequency of 'runts' could be observed between the vaccinated and the placebo-treated group on any of the respective weighing time points. After the overall onset of PCV2 viremia, the frequency of 'runts' was generally low in both treatment groups (3.3-4.7%).

TABLE 1

Comparison of the frequency of 'runts' (pooled data of all three week groups)

| | Before Onset of viremia | | | After Onset of viremia | |
|---|---|---|---|---|---|
| Study week | 0 | 7 | 12 | 17 | 22 |
| CP | 11.51% | 11.94% | 5.68% | 4.72% | 4.53% |
| IVP | 10.84% | 10.46% | 4.78% | 3.36% | 3.27% |
| P | 0.6874 | 0.3728 | 0.4884 | 0.1898 | 0.2259 |

P: p-value of t-test for comparison between groups;
$p > 0.05$ no significant

Impact of Subclinical Infection on Growth Performances

Figure 3:
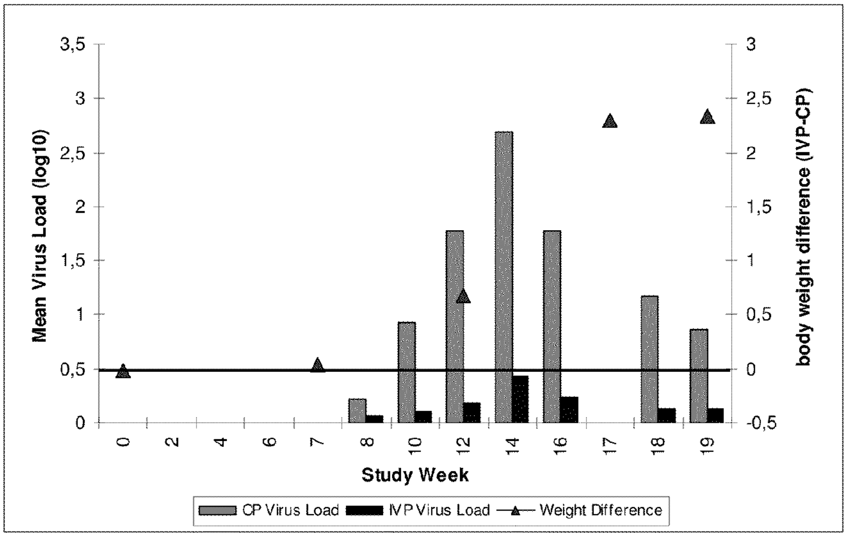
FIG. 3 is a graph illustrating the development of the relative body weight difference (IVP-CP) and of the mean virus load (log 10) over the course of the study.

Body weight gain until study week 17 was 2.36 kg higher and until study week 19 it was 2.39 kg higher in the vaccinated group than in the CP-treated group. As shown in FIG. 3, the body weight difference began to rise slightly at the time of the onset of viremia (study week 12). On study week 17, the difference reached was already 2.36 kg. Due to the higher weight gain, the mean time from weaning to slaughter was 1.9 days shorter for the vaccinated animals than for the CP-treated animals.

TABLE 2

Comparison of Weight gain and ADWG (pooled data of all five week groups)

| | Study week | CP-treated Group (LSMean) | Vaccinated Group (LSMean) | Difference (IVP minus CP) | p-value[1)] |
|---|---|---|---|---|---|
| Weight gain | 0-7 | 20.63 kg | 20.71 kg | 0.08 kg | 0.7166 ns |
| | 0-17 | 76.73 kg | 79.09 kg | 2.36 kg | <0.0001 *** |
| | 0-19 | 86.75 kg | 89.14 kg | 2.39 kg | <0.0001 *** |
| | 12-17 | 29.05 kg | 30.73 kg | 1.68 kg | <0.0001 *** |
| | 7-19 | 66.07 kg | 68.38 kg | 2.31 kg | <0.0001 *** |

[1)]p-value of t-test for comparison between groups, ns: not significant;
* significant, $p \leq 0.05$;
*** significant, $p \leq 0.001$ Duration of Viremia in the Blood When comparing the overall mean and median duration of viremia in the two treatment groups, a significantly longer (p=0.0003) duration of viremia was detected in the CP-treated animals. The IVP group had a mean duration of viremia of 5.8 days while the CP group showed a mean duration of 21.8 days. This corresponds to a reduced duration of viremia by 73% in the IVP group.

TABLE 3

Mean and median duration of viremia

| | Treatment group | Number of pigs | Mean (days) | Median (days) | p-value |
|---|---|---|---|---|---|
| Total | CP | 76 | 21.8 | 14.0 | 0.0003 *** |
| | IVP | 18 | 5.8 | 0.0 | |
| | IVP minus CP | | −16.0 | −14.0 | |

P: p-value of t-test for comparison between groups
ns: not significant, $p > 0.05$;
* significant, $p \leq 0.05$ Conclusion The study has been conducted on a farm that shifted from an acute to a chronic status with sub-clinical infection shortly before the implementation of the study. The viral load of the study animals during the study confirmed that assumption. Very few study animals (<2.19%) had viral load in serum above the "clinical cut-off" of $10^6$/ml genomic copies.

The vaccination succeeded in lowering tremendously the percentage of infected animals in the vaccinated group. Therefore, the vaccination enabled the comparison of non-infected animals (vaccinated group) with sub-clinically infected animals (placebo group). Vaccinated animals demonstrated better growth performances than sub-clinically infected animals. On study week 17, the difference reached already 2.36 kg. Vaccinated animals had a more than 16 day shorter duration of viremia as compared to the non-vaccinated group.

It can be concluded that although infected animals remained apparently healthy, PCV2 subclinical infection can have a relevant negative impact on the growth performances.

The invention claimed is:

1. A method for the prophylaxis and treatment of a sub-clinical PCV2 infection in an pig or a group of pigs, comprising the step of once administering an immunogenic composition comprising a PCV2 ORF2 protein to a pig or group of pigs in need of such administration wherein the sub-clinical PCV2 infection is characterized by individual infected pigs that are infected with PCV2 but are clinically asymptomatic and that have at or below $10^6$ viral copies of PCV2 per ml of serum for at least 6 weeks in the absence of one or more clinical symptoms of PCVD.

2. The method according to claim 1, wherein the sub-clinical PCV2 infection is characterized by a maximum of 20% of pigs within a group of pigs with viral titers above $10^6$ genomic copies per ml serum.

3. The method according to claim 1, wherein the sub-clinical PCV2 infection is characterized by no morbidity or a low morbidity rate of less than 25% of the PCV2 positive pigs within a group of pigs.

4. The method according to claim 1, wherein the sub-clinical PCV2 infection is further characterized by low mortality rate of less than 20% of the PCV2 positive pigs within a group of pigs.

5. The method according to claim 1, wherein said PCV2 ORF2 protein comprises a polypeptide selected from the group consisting of:

i. a polypeptide comprising the sequence of SEQ ID NO. 5, SEQ ID NO. 6, or SEQ ID NO. 11;

ii. a polypeptide having at least 80% sequence homology with the polypeptide of i;

iii. a polypeptide that is encoded by a DNA comprising the sequence of SEQ ID NO. 3 or SEQ ID NO. 4; or iv. a polypeptide that is encoded by a polynucleotide having at least 80% sequence homology with the polynucleotide of iii.

6. The method according to claim 1, wherein said PCV-2 ORF2 protein is a recombinant baculovirus expressed ORF-2 protein of PCV2.

7. The method according to claim 1, wherein said PCV2 ORF2 protein is included in Ingelvac® CircoFLEX™.

8. A method of reducing an impact of PCV2 sub-clinical infection, wherein the sub-clinical PCV2 infection is characterized by individual infected pigs that are infected with PCV2 but are clinically asymptomatic and that have at or below $10^6$ viral copies of PCV2 per ml of serum for at least 6 weeks in the absence of one or more clinical symptoms of PCVD, said impact being selected from the group consisting of reduction of viral load, reduction of the proportion of PCV2 positive animals with $10^6$ genomic copies, duration of viremia, and combinations thereof, said method comprising the step of once administering an immunogenic composition comprising a PCV2 ORF2 protein to a pig in need of such administration.

9. The method according to claim 8, wherein said PCV2 ORF2 protein comprises a polypeptide selected from the group consisting of:

i. a polypeptide comprising the sequence of SEQ ID NO. 5, SEQ ID NO. 6, or SEQ ID NO. 11;

ii. a polypeptide having at least 80% sequence homology with the polypeptide of i;

iii. a polypeptide that is encoded by a DNA comprising the sequence of SEQ ID NO. 3 or SEQ ID NO. 4; or iv. a polypeptide that is encoded by a polynucleotide having at least 80% sequence homology with the polynucleotide of iii.

10. The method according to claim 8, wherein said PCV-2 ORF2 protein is a recombinant baculovirus expressed ORF-2 of PCV2.

11. The method according to claim 8, wherein said PCV2 ORF2 protein is included in Ingelvac® CircoFLEX™.

12. The method of claim 8, wherein the step of administering an immunogenic composition comprises a single dose of 0.2 μg to about 400 μg/dose PCV2 ORF2 protein.

13. A method for the reduction of the number of pigs with viral load above $10^6$ genomic copies per ml serum in at least 80% of the animals in a group of pigs (herds) sub-clinically infected with PCV2, wherein the sub-clinical PCV2 infection is characterized by individual infected pigs that are infected with PCV2 but are clinically asymptomatic and that have at or below $10^6$ viral copies of PCV2 per ml of serum for at least 6 weeks in the absence of one or more clinical symptoms of PCVD, comprising the step of once administering an immunogenic composition comprising 0.2 μg to about 400 μg/dose PCV2 ORF2 protein or an immunogenic composition comprising a PCV2 antigen to a group of pigs in need of such administration.

14. The method according to claim 13, wherein said PCV2 ORF2 protein comprises a polypeptide selected from the group consisting of:

an ORF2 protein comprising a polypeptide selected from the group consisting of:

i. a polypeptide comprising the sequence of SEQ ID NO. 5, SEQ ID NO. 6, or SEQ ID NO. 11;

ii. a polypeptide having at least 80% sequence homology with the polypeptide of i;

iii. a polypeptide that is encoded by a DNA comprising the sequence of SEQ ID NO. 3 or SEQ ID NO. 4; or iv. a polypeptide that is encoded by a polynucleotide having at least 80% sequence homology with the polynucleotide of iii.

15. The method according to claim 13, wherein said PCV-2 ORF2 protein is a recombinant baculovirus expressed ORF-2 of PCV2.

16. The method according to claim 13, wherein the PCV2 ORF2 protein is included in Ingelvac® CircoFLEX™.

17. The method of claim 13, said immunogenic composition further comprising a polymer of acrylic or methacrylic acid.

* * * * *